United States Patent
Weston

(10) Patent No.: US 7,846,141 B2
(45) Date of Patent: Dec. 7, 2010

(54) REDUCED PRESSURE TREATMENT SYSTEM

(75) Inventor: Richard Scott Weston, Carlsbad, CA (US)

(73) Assignee: Bluesky Medical Group Incorporated, Memphis, TN (US)

( * ) Notice: Subject to any disclaimer, the term of this patent is extended or adjusted under 35 U.S.C. 154(b) by 1307 days.

(21) Appl. No.: 10/652,100

(22) Filed: Aug. 28, 2003

(65) Prior Publication Data

US 2004/0073151 A1 Apr. 15, 2004

Related U.S. Application Data

(60) Provisional application No. 60/430,827, filed on Dec. 4, 2002, provisional application No. 60/407,783, filed on Sep. 3, 2002.

(51) Int. Cl.
*A61F 15/00* (2006.01)
(52) U.S. Cl. .......................... 604/313; 602/53
(58) Field of Classification Search ................. 604/313, 604/315, 327, 541; 602/48–56
See application file for complete search history.

(56) References Cited

U.S. PATENT DOCUMENTS

| | | |
|---|---|---|
| 765,746 A | 7/1904 | Miner |
| 846,674 A | 2/1907 | Funk |
| 1,355,679 A | 10/1920 | McConnell |
| 1,355,846 A | 10/1920 | Rannells |
| 1,385,346 A | 7/1921 | Taylor |
| 1,585,104 A | 5/1926 | Montgomery |
| 1,732,310 A | 10/1929 | Naibert |
| 1,863,534 A | 6/1932 | Odell |
| 1,936,129 A | 11/1933 | Fisk |
| 2,122,121 A | 6/1938 | Tillotson |
| 2,232,254 A | 2/1941 | Morgan |

(Continued)

FOREIGN PATENT DOCUMENTS

CA 2049948 C 10/1990

(Continued)

OTHER PUBLICATIONS

Arnljots et al., "Irrigation Treatment in Split-Thickness Skin Grafting of Intractable Leg Ulcers," Scandinavian Journal of Plastic and Reconstructive Surgery, 1985, vol. 19, pp. 211-213.

(Continued)

*Primary Examiner*—Tatyana Zalukaeva
*Assistant Examiner*—Lynne Anderson
(74) *Attorney, Agent, or Firm*—Knobbe, Martens, Olson & Bear LLP

(57) ABSTRACT

A wound treatment apparatus is provided for treating tissue damage, which comprises a fluid impermeable wound cover sealed over a site for purposes of applying a reduced pressure to the site. The apparatus also includes a cover with protrusions on its surface for purposes of monitoring pressure at the site. An absorbable matrix may be placed in the site of a wound to encourage tissue growth into the matrix. Temperature of the site may be monitored using a layer of temperature sensitive material and temperature sensors connected to an alarm and recording device. A vacuum pump supplies suction within the wound cover over the treatment site. A portable version of the wound treatment apparatus is also provided. Finally, a method for treating wounds using reduced pressure is provided.

68 Claims, 7 Drawing Sheets

U.S. PATENT DOCUMENTS

| | | |
|---|---|---|
| 2,280,915 A | 4/1942 | Johnson |
| 2,338,339 A | 1/1944 | La Mere et al. |
| 2,366,799 A | 1/1945 | Luisada |
| 2,367,690 A | 1/1945 | Purdy |
| 2,547,758 A | 4/1951 | Keeling |
| 2,910,763 A | 8/1955 | Lauterbach |
| 3,026,874 A | 11/1959 | Stevens |
| 2,969,057 A | 1/1961 | Simmons |
| 3,026,526 A | 3/1962 | Montrose |
| 3,042,041 A | 7/1962 | Jascalevich |
| 3,217,707 A | 11/1965 | Werding |
| 3,238,937 A | 3/1966 | Stein |
| 3,286,711 A | 11/1966 | MacLeod |
| 3,315,665 A | 4/1967 | MacLeod |
| 3,367,332 A | 2/1968 | Groves |
| 3,465,748 A | 9/1969 | Kravchenko |
| 3,478,736 A | 11/1969 | Roberts et al. |
| 3,486,504 A | 12/1969 | Austin, Jr. |
| 3,568,675 A | 3/1971 | Harvey |
| 3,572,340 A | 3/1971 | Lloyd et al. |
| 3,610,238 A | 10/1971 | Rich, Jr. |
| 3,682,180 A | 8/1972 | McFarlane |
| 3,712,298 A | 1/1973 | Snowdon et al. |
| 3,794,035 A | 2/1974 | Brenner |
| 3,826,254 A | 7/1974 | Mellor |
| 3,859,989 A | 1/1975 | Spielberg |
| 3,874,387 A | 4/1975 | Barbieri |
| 3,896,810 A | 7/1975 | Akiyama |
| 3,908,664 A | 9/1975 | Loseff |
| 3,938,540 A | 2/1976 | Holbrook et al. |
| 3,954,105 A | 5/1976 | Nordby et al. |
| 3,961,625 A | 6/1976 | Dillon |
| 3,988,793 A | 11/1976 | Abitbol |
| 3,993,080 A | 11/1976 | Loseff |
| RE29,319 E | 7/1977 | Nordby et al. |
| 4,080,970 A | 3/1978 | Miller |
| 4,112,947 A | 9/1978 | Nehring |
| 4,149,541 A | 4/1979 | Gammons et al. |
| 4,169,563 A | 10/1979 | Leu |
| 4,172,455 A | 10/1979 | Beaussant |
| 4,224,945 A | 9/1980 | Cohen |
| 4,250,882 A | 2/1981 | Adair |
| 4,256,109 A | 3/1981 | Nichols |
| 4,261,363 A | 4/1981 | Russo |
| 4,275,721 A | 6/1981 | Olson |
| 4,297,995 A | 11/1981 | Golub |
| 4,373,519 A | 2/1983 | Errede et al. |
| 4,382,441 A | 5/1983 | Svedman |
| 4,392,853 A | 7/1983 | Muto |
| 4,419,097 A | 12/1983 | Rowland |
| 4,444,548 A | 4/1984 | Anderson et al. |
| 4,459,139 A | 7/1984 | vonReis et al. |
| 4,465,485 A | 8/1984 | Kashmer et al. |
| 4,469,092 A | 9/1984 | Marshall et al. |
| 4,475,909 A | 10/1984 | Eisenberg |
| 4,480,638 A | 11/1984 | Schmid |
| 4,525,166 A | 6/1985 | Leclerc |
| 4,527,064 A | 7/1985 | Anderson |
| 4,540,412 A | 9/1985 | Van Overloop |
| 4,543,100 A | 9/1985 | Brodsky |
| 4,573,965 A | 3/1986 | Russo |
| 4,605,399 A | 8/1986 | Weston et al. |
| 4,608,041 A | 8/1986 | Nielsen |
| 4,624,656 A | 11/1986 | Clark et al. |
| 4,640,688 A | 2/1987 | Hauser |
| 4,710,165 A | 12/1987 | McNeil et al. |
| 4,738,249 A | 4/1988 | Linman et al. |
| 4,743,232 A | 5/1988 | Kruger |
| 4,753,231 A | 6/1988 | Lang et al. |
| 4,759,354 A | 7/1988 | Quarfoot |
| 4,764,167 A | 8/1988 | Tu |
| 4,765,316 A | 8/1988 | Marshall |
| 4,778,456 A | 10/1988 | Lokken |
| 4,820,265 A | 4/1989 | DeSatnick et al. |
| 4,820,284 A | 4/1989 | Hauri |
| 4,834,110 A | 5/1989 | Richard |
| 4,836,192 A | 6/1989 | Abbate |
| 4,838,883 A | 6/1989 | Matsuura |
| 4,840,187 A | 6/1989 | Brazier |
| 4,841,962 A | 6/1989 | Berg et al. |
| 4,851,545 A | 7/1989 | Song et al. |
| 4,863,449 A | 9/1989 | Therriault et al. |
| 4,878,901 A | 11/1989 | Sachse |
| 4,906,233 A | 3/1990 | Moriuchi et al. |
| 4,917,112 A | 4/1990 | Kalt |
| 4,921,488 A | 5/1990 | Maitz et al. |
| 4,921,492 A | 5/1990 | Schultz et al. |
| 4,925,447 A | 5/1990 | Rosenblatt |
| 4,931,519 A | 6/1990 | Song et al. |
| 4,941,882 A | 7/1990 | Ward et al. |
| 4,950,483 A | 8/1990 | Ksander et al. |
| 4,953,565 A | 9/1990 | Tachibana et al. |
| 4,969,880 A | 11/1990 | Zamierowski |
| 4,969,881 A | 11/1990 | Viesturs |
| 5,035,884 A | 7/1991 | Song et al. |
| 5,086,764 A | 2/1992 | Gilman |
| 5,100,396 A | 3/1992 | Zamierowski |
| 5,106,362 A | 4/1992 | Gilman |
| 5,113,871 A | 5/1992 | Viljanto et al. |
| 5,149,331 A | 9/1992 | Ferdman et al. |
| 5,184,077 A | 2/1993 | Day et al. |
| 5,228,431 A | 7/1993 | Giarretto |
| 5,261,893 A | 11/1993 | Zamierowski |
| 5,307,791 A | 5/1994 | Senoue et al. |
| 5,462,514 A | 10/1995 | Harris |
| 5,489,280 A | 2/1996 | Russell |
| 5,549,584 A | 8/1996 | Gross |
| 5,618,556 A | 4/1997 | Johns et al. |
| 5,636,643 A | 6/1997 | Argenta et al. |
| 5,645,081 A | 7/1997 | Argenta et al. |
| 5,701,917 A | 12/1997 | Khouri |
| 5,716,411 A | 2/1998 | Orgill et al. |
| 5,795,584 A * | 8/1998 | Totakura et al. ............. 424/426 |
| 5,827,246 A | 10/1998 | Bowen |
| 5,830,496 A | 11/1998 | Freeman |
| 5,893,368 A | 4/1999 | Sugerman |
| 5,938,626 A | 8/1999 | Sugerman |
| 6,045,541 A | 4/2000 | Matsumoto et al. |
| 6,117,444 A | 9/2000 | Orgill et al. |
| 6,135,116 A | 10/2000 | Vogel et al. |
| D434,150 S | 11/2000 | Tumey et al. |
| 6,142,982 A | 11/2000 | Hunt |
| 6,176,307 B1 | 1/2001 | Danos et al. |
| 6,287,521 B1 | 9/2001 | Quay et al. |
| 6,402,724 B1 | 6/2002 | Smith et al. |
| 6,458,109 B1 | 10/2002 | Henley et al. |
| 6,465,708 B1 | 10/2002 | Augustine |
| 6,471,685 B1 | 10/2002 | Johnson |
| 6,482,491 B1 * | 11/2002 | Samuelsen et al. ......... 428/40.1 |
| 6,595,949 B1 | 7/2003 | Shapiro |
| 6,695,823 B1 | 2/2004 | Lina et al. |
| 6,936,037 B2 | 8/2005 | Bubb et al. |
| 6,951,553 B2 | 10/2005 | Bubb et al. |
| 6,979,324 B2 | 12/2005 | Byborddi et al. |
| 6,988,423 B2 | 1/2006 | Bolam et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,735 B2 | 10/2006 | Weston |
| 7,198,046 B1 | 4/2007 | Argenta et al. |

| | | | |
|---|---|---|---|
| 7,216,651 B2 | 5/2007 | Argenta et al. | |
| 7,322,971 B2 | 1/2008 | Shehada | |
| 7,381,859 B2 | 6/2008 | Hunt et al. | |
| 7,494,482 B2 | 2/2009 | Orgill et al. | |
| 2001/0029956 A1 | 10/2001 | Argenta et al. | |
| 2001/0043943 A1 | 11/2001 | Coffey | |
| 2002/0065494 A1 | 5/2002 | Lockwood et al. | |
| 2002/0068913 A1 | 6/2002 | Fleischmann | |
| 2002/0115952 A1 | 8/2002 | Johnson et al. | |
| 2002/0143286 A1 | 10/2002 | Tumey | |
| 2002/0161346 A1 | 10/2002 | Lockwood et al. | |
| 2002/0183702 A1 | 12/2002 | Henley et al. | |
| 2002/0198503 A1 | 12/2002 | Risk et al. | |
| 2002/0198504 A1 | 12/2002 | Risk et al. | |
| 2003/0014025 A1* | 1/2003 | Allen et al. | 604/361 |
| 2003/0040687 A1 | 2/2003 | Boynton et al. | |
| 2003/0050594 A1 | 3/2003 | Zamierowski | |
| 2003/0108587 A1 | 6/2003 | Orgill et al. | |
| 2003/0125646 A1 | 7/2003 | Whitlock | |
| 2003/0225347 A1 | 12/2003 | Argenta et al. | |
| 2004/0054338 A1 | 3/2004 | Bybordi et al. | |
| 2004/0073151 A1 | 4/2004 | Weston | |
| 2004/0127863 A1 | 7/2004 | Bubb et al. | |
| 2005/0148913 A1 | 7/2005 | Weston | |
| 2005/0203452 A1 | 9/2005 | Weston et al. | |
| 2005/0222527 A1 | 10/2005 | Miller et al. | |
| 2005/0222528 A1 | 10/2005 | Weston | |
| 2005/0222544 A1 | 10/2005 | Weston | |
| 2005/0261615 A1 | 11/2005 | Weston | |
| 2005/0261642 A1 | 11/2005 | Weston | |
| 2005/0261643 A1 | 11/2005 | Bybordi et al. | |
| 2007/0066945 A1 | 3/2007 | Martin | |
| 2007/0239139 A1 | 10/2007 | Weston et al. | |
| 2007/0293830 A1 | 12/2007 | Martin | |
| 2008/0306456 A1 | 12/2008 | Riesinger | |
| 2009/0105671 A1 | 4/2009 | Daggar et al. | |

FOREIGN PATENT DOCUMENTS

| | | | |
|---|---|---|---|
| CA | 2369000 A1 | 10/1990 | |
| CA | 2103033 C | 11/1992 | |
| CA | 2414393 A1 | 11/1992 | |
| CA | 2121688 C | 5/1993 | |
| CA | 2115951 A1 | 8/1994 | |
| CA | 2157772 C | 9/1995 | |
| CA | 2198243 A1 | 2/1996 | |
| CA | 2237606 A1 | 5/1997 | |
| CA | 2238413 A1 | 5/1997 | |
| CA | 2551340 A1 | 5/1997 | |
| CA | 2272399 A1 | 11/1997 | |
| CA | 2280817 A1 | 2/1998 | |
| CA | 2267312 A1 | 4/1998 | |
| CA | 2272372 A1 | 5/1998 | |
| CA | 2303085 A1 | 3/1999 | |
| CA | 2471780 A1 | 3/1999 | |
| CA | 2347115 A1 | 4/2000 | |
| CA | 2367460 A1 | 10/2000 | |
| CA | 2369022 C | 10/2000 | |
| CA | 2369024 A1 | 10/2000 | |
| CA | 2390513 A1 | 5/2001 | |
| CA | 2408305 A1 | 11/2001 | |
| CA | 2351342 A1 | 6/2002 | |
| CA | 2442724 A1 | 10/2002 | |
| CA | 2432293 A1 | 2/2003 | |
| CA | 2458285 A1 | 3/2003 | |
| CA | 2483654 A1 | 11/2003 | |
| CA | 2490027 A1 | 12/2003 | |
| CA | 2368085 C | 5/2006 | |
| DE | 561757 | 10/1932 | |
| DE | 847475 | 8/1952 | |
| DE | 2809828 | 9/1978 | |
| DE | 4111122 | 4/1993 | |
| EP | 0 777 504 B1 | 8/1995 | |
| EP | 0 853 950 B1 | 8/1995 | |
| EP | 1 897 569 B1 | 8/2002 | |
| FR | 1163907 | 5/1958 | |
| GB | 114754 | 4/1918 | |
| GB | 641061 | 8/1950 | |
| GB | 1273342 | 5/1972 | |
| GB | 2041756 | 9/1980 | |
| GB | 2195255 A | 4/1988 | |
| GB | 2235877 A | 9/1989 | |
| RU | 240188 | 3/1969 | |
| WO | WO 87/04626 | 8/1987 | |
| WO | WO 90/10424 | 9/1990 | |
| WO | WO 90/11795 | 10/1990 | |
| WO | WO 91/00718 | 1/1991 | |
| WO | WO 91/16030 | 10/1991 | |
| WO | WO 92/19313 | 11/1992 | |
| WO | WO 92/20299 | 11/1992 | |
| WO | WO 94/20041 | 9/1994 | |
| WO | WO 96/05873 | 2/1996 | |

OTHER PUBLICATIONS

Bagautdinov, "Variant of External Vacuum Aspiration in the Treatment of Purulent Diseases of Soft Tissues," Current Problems in Modern Clinical Surgery, 1986, 4 pages.

Boretos, "Cellular Polymers for Medical Use: The Vital Role of Porosity and Permeability," Cellular Polymers, 1984, vol. 3, pp. 345-358.

Chardack et al., "Experimental Studies on Synthetic Substitutes for Skin and Their Use in the Treatment of Burns," Annals of Surgery, 1962, vol. 155, No. 1, pp. 127-139.

Dilmaghani et al., "A Method for Closed Irrigation and Suction Therapy in Deep Wound Infections," Journal of Bone and Joint Surgery, 1969, vol. 51-A, No. 2, pp. 323-342.

International Standard ISO 10079-1, First Edition, May 15, 1991, 2 pages.

Meyer et al., "Bier's Hyperemic Treatment in Surgery, Medicine, and the Specialties: A Manual of Its Practical Application," 1908, 222 pages.

Orringer et al., "Management of Wounds in Patients with Complex Enterocutaneous Fistulas," Surgery, Gynecology, & Obstetrics, Jul. 1987, vol. 165, pp. 79-80.

Robertson, "The Influence upon Wound Contraction of a Negative Interstitial Fluid Pressure Within Granulation Tissue," Journal of Anatomy, 1969, vol. 105, No. 1, pp. 189.

Teder, et al., "Continuous Wound Irrigation in the Pig," Journal of Investigative Surgery, 1990, vol. 3, pp. 399-407.

Tennant, "The Use of Hyperemia in the Postoperative Treatment of Lesions of the Extremities and Thorax," Journal of the American Medical Association, 1915, vol. 64, No. 19, pp. 1548-1549.

Greene, M. A., et al. Laparotomy Wound Closure with Absorable Polyclycolic Acid Mesh, Surgery, Gynecology and Obsterics Mar. 1993; 176: 213-218.

Meyer and Schmieden, Bier's Hyperemic Treatment, Published 1908 W. B. Saunders Company, 44-65.

U.S. Appl. No. 12/375,191, filed Jan. 26, 2009) and its ongoing prosecution history, including without limitation Office Actions, Amendments, Remarks, and any other potentially relevant documents, Richard S. Weston, et al.

U.S. Appl. No. 12/186,424, filed Aug. 5, 2008) and its ongoing prosecution history, including without limitation Office Actions, Amendments, Remarks, and any other potentially relevant documents, Kenneth P. Krohn.

Blumberg, et al., "The Effect of Specific Compression on Soft-Tissue Response to Formalinized PVA (Ivalon) Sponge: A Critical Evaluation," *Annals Surg.*, Mar. 1960, 151(3), 409-418.

Morykwas, M. J., et al., "Vacuum-Assisted Closure: A New Method for Wound Control and Treatment: Animal Studies and Basic Foundation," *Annals of Plastic Surgery* 38 (1997) 553-562.

Schein et al., "The 'Sandwich Technique' in the Management of the Open Abdomen," *British Journal of Surgery*, 1986, vol. 73, May, pp. 369-370.

Thomas, Stephen "Wound Management and Dressings" 35-42 (1990).
Chariker, Mark E., et al, "Effective Management of Incisional and Cutaneous Fistulae with Closed Suction Wound Drainage," Contemporary Surgery, vol. 34, p. 59 (Jun. 1989).
Biblbhimer, Helen L., "Dealing With a Wound that Drains 1.5 Liters a Day," RN, p. 21 (Aug. 1986).
Wooding-Scott, Margaret, et al, "No Wound is too Big for Resourceful Nurses," RN, p. 22 (Dec. 1988).
Garcia-Renaldi, Raul, et al, "Improving the Efficiency of Wound Drainage Catheters," Journal of Surgery (?) vol. 130, p. 372 (Sep. 1975).
Schwab, Peter M., and Kelly, Keith A., "Primary Closure of Perinial Wound After Proctectomy," Mayo Clinic Procedures (?), vol. 49, p. 176 (Mar. 1974).
Ramirez, Oscar M., et al, "Optimal Wound Healing Under Up-Site TM Dressing," Ideas and Innovations (?), vol. 73, No. 3, p. 479, May 9, 1983, pp. 474-475.
Raffl, Arthur B., "Use of Negative Pressure Under Skin Flaps After Radical Mastectomy," Dept. of Surgery, State Univ. of N.Y., College of Medicine, Syracuse, N.Y., Submitted for publication Apr. 1953, p. 1048, USA.
Knight, Marie Ray, "A Second Skin for Patents With Large Draining Wounds," Nursing, Jan. 1976, p. 37.
3M Health Care, Controlling the Risk of Surgical Site Infections after Cardiovascular Procedures: The Importance of Providing a Sterile Surface, Brochure, St. Paul, MN and London, Ontario, Canada, 1997, 8 pages.
Aeros, "Moblvac II.". 1 page, Aeros Instruments, Inc., Northbrook IL, Oct. 1988.
Aeros, Aeros Instruments, Inc. 1111 Lakeside Dr., Gurnee, IL 60031. Aug. 1993. "Care-E-Vac."
Aeros, Aeros Insturments, Inc. 3411 Commercial Ave., Northbrook, IL 60062. Oct. 1988. Part No. 1504-02 7M. "Instavac Aspirator."
Agarwala, S., et al., Use of Mini-Vacuum Drains in Small Surgical Wounds, *Plastic and Reconstructive Surgery*, Apr. 1998, 101(5), 1421-1422 (*Correspondence*).
Agrama, H.M., Functional Longevity of Intraperiotoneal Drains, *Amer. Journ. of Surg.*, Sep. 1976, 132, 418-421.
A. Harle, Z. Orthop., 127: 513-517 (1989), "Schwachstellen herkommlicher Drainagen."
Alexander, J. Wesley, "Prevention of Wound Infections," The American Journal of Surgery, Jul. 1976, pp. 59-63, vol. 132, USA.
Alper, J.C., et al., An Effective Dressing for a Large, Draining Abdominal wound, *RN*, Dec. 1988, 24-25.
Alper, J.C., et al., Moist Wound Healing under a Vapor Permeable Membrane, *Journ. of Amer. Acad. of Derm.*, Mar. 1983, 8(3), 347-353.
Alper, Joseph, C., "Recent Advances in Moist Wound Healing," Southern Medical Journal, Nov. 1988, pp. 1398-1404, vol. 79, No. 11 USA.
Ashrafov, A.A. and K.G. Ibishov, An Experimental and Clinical Validation for the Use of a Collagen Sponge for Treating the Suppurative-Inflammatory Complications of Wound Healing in Emergency Abdominal Surgery, *PubMed, Abs. Downloaded from Internet*, Apr. 24, 2006.
Aubrey, D.A., et al., Treatment of Wound after Proctectomy by Intermittent Irrigation, *Arch. Surg.*, Oct. 1984, 119, 1141-1144.
Author Unknown, A Sensational Medical discovery, *Brit. Journ. Nurs.*, Jul. 15, 1911, 42.
Author Unknown, Article Excerpt, *Lancet*, Jun. 14, 1952, 1175-1176.
Author Unknown, Assessing the Patient with a Fistula or Draining Wounds, *Nursing*, Jun. 1980, 49-51.
Author Unknown, Chart: Influence of Wound Closure on Healing of Perineal Wound after Abdominoperineal Resection or Total Proctocolectomy, excerpt faxed Jan. 23, 2006.
Author Unknown, Hanbok för Hälso-Och Sjukvårdsarbete Lokal Anvisning för Landstinget Sörmland, Jan. 2001, 7 pgs, (in Swedish), Downloaded from Internet http://www.landstinget.sormland.se, Aug. 14, 2001.
Author Unknown, The Bier Treatment, *Brit. Journ. Nurs.*, Jun. 6, 1908, 452.

Author Unknown, Science, Sep. 1992, p. 42, "The Not-So-Bald-Truth."
Author Unknown, Title N/A, *Brit. Journ. Nurs.*, Nov. 4, 1911, 368.
Author Unknown, Tuberculous Joints, *Nursing record & Hospital World*, Apr. 28, 1894, 280.
Author Unknown, Wound Suction: Better Drainage with Fewer Problems, *Nursing* Oct. 1975, 52-53.
Author Unknown, "Wound Suction", *Nursing*, Oct. 1975, pp. 52-53, USA.
Avocat, C. et al., Nouvelle Presentation de Material Pour Drainage de Redon et Jost, *La Nouvelle Press Medicale*, Jun. 26, 1976, 5(6), 1644-1645 (in French).
Ayoub, M.H. and G. C. Bennet, A Study of Cutaneous and Intracompartmental Limb Pressures Associated with the Combined Use of Tourniquets and Plaster Casts, Abs., *Proc. and Reports of Univ., Colleges, Councils, Assoc., and Societies*, 68-B:3, May 1986, 497.
Baldwin, J.F., Ed., The Columbus Medical Journal, Columbus, Ohio, 1887, V., 561.
Barbul, A., et al., Eds., Clinical and Experimental Approaches to Dermal and Epidermal Repair, Normal and Chronic Wounds, Progress in Clin. and Biol. Res., vol. 365, *Proc. of the 3rd Intnl. Symp. on Tissue Repair*, Miami, FL, Jan. 10-14, 1990, *Abs*.
Bar-El, Y. et al., Potentially dangerous Negative Intrapleural pressures Generated by Ordinary Pleural Drainage Systems, *Chest*, Feb. 2001, 119(2), 511-514.
Barker, D.E., et al., Vacuum Pack Technique of Temporary Abdominal Closure: A 7-Year Experience with 112 Patients, *Journ. of Trauma: Injury and Critical Care*, Feb. 2000, 4892), 201-207.
Bascom, J., Pilonidal Sinus, *Current Therapy in Colon and Rectal Surgery*, 1990, 1-8.
Benjamin, P.J., Faeculent Peritonitis: A Complication of Vacuum Drainage, *Br. J. Surg.*, 1980, 67, 453-454.
Berman and Fabiano, Closed Suction Drainage, *Orthopedics*, Mar. 1990, 13(3), 310-314.
Berman, A. T., et al., Comparison Between Intermittent (Spring-Loaded) and Continuous Closed Suction Drainage of Orthopedic Wounds: A Controlled Clinical Trial, *Orthopedics*, Mar. 1990, 13(3), 9 pgs.
Besst, J.A., Wound Healing—Intraoperative Factors, *Nursing Clinics of North America*, Dec. 1979, 14(4), 701-712.
Betancourt, Sergio, "A Method of Collecting the Effluent from Complicated Fistual of the Small Intestine," Dept. of Surgery, Allegheny General Hospital, Pittsburgh, p. 375, USA.
Biblehimer, Helen L., "Dealing With a Wound that Drains 1.5 Liters a Day," RN, Aug. 1986, pp. 21 23, USA.
Bier, A., Hyperemia as a Therapeutic Agent, *Ed. Dr. Gustavus M. Blech, A. Robertson & Co.*, Chicago 1905. (the entire reference has been submitted, but pp. 74-85 may be the most relevant).
Bischoff, et al., Vacuum-Sealing Fixation of Mesh Grafts, *Euro. Journ. Plast. Surg.*, Jul. 2003, 26(4), 189-190, *Abs. Downloaded from internet* Apr. 6, 2006.
Bonnema, J., et al., A Prospective Randomized Trial of High Versus Low Vacuum Drainage after Axillary Dissection for Breast Cancer, *Amer. Journ. Surg.*, Feb. 1997, 173, 76-79.
Britton, B.J., et al., A Comparison Between Disposable and Non-Disposable Suction Drainage Units: A Report of a Controlled Trial, *Br. J. Surg.* 1979, 66, 279-280.
Broader, J.H., et al., Management of the Pelvic Space after Proctectomy, *Br. J. Surg.*, 1974, 62, 94-97.
Brubacher, Lynda L., "To Heal a Draining Wound", RN, Mar. 1982, pp. 30-35, USA.
Brummelkamp, W.H., et al, "High-vacuum drainage and primary perineal wound closure in abdominoperineal excision of the rectum", The Netherlands Journal of Surgery, 1991 pp. 236-238, Netherlands.
Bruno, P., The Nature of Wound Healing: Implications for Nursing Practice, *Nursing Clinics of North American*, Dec. 1979, 14(4), 667-682.
Bucalo et al. "Inhibition of Cell Proliferation by Chronic Wound Fluid." Wound Repair and Regeneration. Miami, 1993. pp. 181-186.
Burdette-Taylor, S.R., Use of the Versatile One (V1) for Closed Suction Drainage to Stimulate Closure in Chronic Wounds in Home Care, Case Study Presentation, 2003, 2 pgs.

Bush, G.K., What is a Counter Irritant? Name Any That You Know and the Method of their Application, *Brit. Journ. Nurs.*, Oct. 1927, 232.

Candiani, P., et al., Repair of a Recurrent Urethrovaginal Fistula with an Island Bulbocavernous Musculocutaneous Flap, *Plastic and Reconstructive Surgery*, Dec. 1993, 1393-1394.

Carroll, P.L., The Principles of Vacuum and its Use in the Hospital Environment, 2$^{nd}$ Ed., 1986, 30p.

Chariker, M.E., et al, "Effective Management of Incisional and Cutaneous Fistulae with Closed Suction Wound Drainage," Contemporary Surgery. Jun. 1989, pp. 59-63, vol. 34 USA.

Chua Patel, C.T., et al., Vacuum-Assisted Closure, *AJN*, Dec. 2000, 100(12), 45-49.

Cobb, J.P., Why Use Drains?, *Br. J. Bone Joint Surg.*, Nov. 1990, 72-B(6), 993-995.

Cooper, D.M., Optimizing Wound Healing, *Nursing Clinics of North America*, Mar. 1990, 25(1), 163-179.

Cooper, D.M., Postsurgical Nursing Intervention as an Adjunct to Wound Healing, *Nursing Clinics of North America*, Dec. 1979, 14(4), 713-726.

Cooper, S.M. and E. Young, Topical Negative Pressure, *Commentary, International Journal of Dermatology 2000*, 39, 892-898.

Costunchenok, B.M., et al., Effect of Vacuum on Surgical Purulent Wounds, *Vestnik Chirurgia 1986*, Sep. 18-20 (in Russian with English translation).

Cotton, P.B., et al., Early Endoscopy of Oesophagus, Stomach, and Duodenal Bulb in patients with Haematemesis and Melaena, *Br. Med. Journ.*, Jun. 1973, 2, 505-509.

Crisp, W.J. and A. Gunn, Granuflex Dressings for Closed Surgical Wounds Combined with Suction Drainage, *Annals of the Royal College of Surgeons of England*, 1990, 72, p. 76.

Curtin, L.L., Wound Management: care and Cost—an Overview, *Nursing Management*, Feb. 1984, 15, 22-25.

Davis, J.C. and T.K. Hunt, Eds., Problem Wounds: The Role of Oxygen, Chap. 1, Infection and Oxygen, 1988, 1-15.

Davidov, Y.A., et al. Justifying the Usage of Force Early Secondary Sutures in treatment of Purulent Wounds by the Vacuum Therapy, *Vestnik Chirurgia 1990*, March Edition, 126-129 (*in Russian with English translation*).

Davidov, Y.A., et al., Concept of Clinico-Biological Management of Wound Process in Treatment of Purulent Wounds with the Help of Vacuum Therapy, *Vestnik Chirurgia 1991*, February Edition, 132-135 (*in Russian with English translation*).

Davidov, Y.A., et al., The Bacteriological & Cytological Assessment of Vacuum Therapy of Purulent Wounds, *Vestnik Chirurgia 1988*, October Edition 48-52 (in Russian with English translation). 1987.

Davidov, Y.A., et al., Vacuum Therapy in the Treatment of Purulent Lactational Mastitis, *Vestnik Chirurgia, Grexova 1986*, September Edition, 66-70 (in Russian with English translation).

Davidov et al. "Pathogenic Mechanism of the Effect of Vacuum Therapy on the Course of the Wound Process" Dec. 1986.

Dillon, Angiology, The Journal of Vascular Diseases, pp. 47-55, Jan. 1986, "Treatment of Resistant Venous Statis Ulcers and Dermatitis with the End-Diastolid Pneumatic Compression Boot."

Domkowski, P.W., et al., Evaluation of Vacuum-Assisted Closure in the Treatment of Poststernotomy Mediastinitis, *Journ. Of Thorac. And Cardiovascular Surg.*, Aug. 2003, 126(2), 386-390.

Doss, Mirko, et al., Vacuum-Assisted Suction Drainage Versus Conventional Treatment in the Management of Poststernotomy Osteomyelitis, *Euro. Journ. Cardio-Thoracic. Surg. 22* ((2002) 934-938.

Draper, J., Make the Dressing Fit the Wound, *Nursing Times*, Oct. 9, 1985, 32-35.

Dunbar, J.M., State What You Have Learned Recently on the Up-to-Date Care of Wounds, *Brit. Journ. Nurs.*, Dec. 1941, 200.

Dunlop, M.G, et al. Vacuum Drainage of Groin Wounds after Vascular Surgery: A Controled Trial, Br. J. Surg., May 1990, 77, 562-563.

Eaglstein, W.H., et al., Wound Dressings: Current and Future, *Clin. And Exper. Approaches to Dermal and Epidermal Repair: Normal and Chronic Wounds*, 1991, 257-265.

Ecri, Target Report, Negative Pressure Wound Therapy for Chronic Wounds, Jan. 24, 2006, 1-7, Downloaded from internet, http://www.target.ecri.org/summary/detail.aspx?dox_id=1155.

Eisenbud, D.E., Modern Wound Management, *Anadem Publishing*, Chap. 16, 109-116.

Ellingwood, F., Ellingwood's Therapeutist, Jun. 14, 1908, 2(6), 32-33.

Elwood, E.T., and D.G. Bolitho, Negative-Pressure Dressings in the Treatment of Hidradenitis Suppurative, *Annals of Plastic Surgery*, Jan. 2001, 46(1), 49-51.

Engdahl, O. and J. Boe, Quantification of Aspirated Air Volume reduces Treatment Time in Pneumothorax, *Eur. Respir, J.*, 1990, 3, 649-652.

Engdahl, O., et al., Treatment of Pneumothorax: Application of a Technique which Quantifies Air Flow Through the Chest Drain, *Adv. In Therapy*, May/Jun. 1988, 5(3), 47-54.

Erichsen, J.E., Science and Art of Surgery, *London: Longmans, Green, and Co.*, 1895, vol. 1, 258-259, and p. 289.

Fabian, T.S., The Evaluation of Subatmospheric Pressure and Hyperbaric Oxygen in Ischemic Full-Thickness Would Healing, *Ischemic Full-Thickness Would Healing*, Dec. 2000, 66(12), 1136-1143.

Falanga, Vincent, "Growth Factors and Chronic Wounds: The need to Understand the Microenvironment." Journal of Dermatology, vol. 19: 667-672, 1992.

Fay, M.F., Drainage Systems: Their Role in Wound Healing, *AORN Journal*, Sep. 1987, 46(3), 442-455.

Fellin, R., Managing Decubitus Ulcers, *Nursing Management*, Feb. 1984, 29-30.

Fingerhut, A., et al., Passive vs. Closed Suction drainage after Perineal Wound Closure Following Abdominoperineal Rectal Excision for Carcinoma, *Dis Colon Rectum*, Sep. 1995, 926-932.

Finley, John M., "Practical Wound Management," pp. 45, 127, 143, 149, 207, 1981.

Firlit, C.F. and J.R. Canning, Surgical Wound Drainage: A Simple Device for Collection, *Journ. of Urology*, Aug. 1972, 108, p. 327.

Fisher, Jack, and R. W. Bert, Jr., A Technique for Skin Grafting Around Abdominal Wall Fistulas, *Annals of Plastic Surgery*, 11:6, Dec. 1983, 563-564.

Flanagan, et al., Optional Sump: Novel Use of Triple Lumen Closed Drainage System, *Anz. J. Surg.*, Nov. 2002, 72(11), 806-807, *Abs. Downloaded from internet* Nov. 30, 2003.

Fleischmann, W. Acta Orthopaedical Belgica. vol. 58, Suppl. I-1992 "Treatment of Bone and Soft Tissue Defects in Infected Nonunion."

Fleischmann, W. Unfall Chirurg. Springer-Variag 1993. "Vakuumversiegelung zur Behandlung des Weichteilschadens bei offenen Frakturen." (English abstract, no English translation).

Fleischmann, W. Wund Forum Spezial. IHW '94. "Vakuumversiegelung zur Behandlung von Problemwunden" (with English translation: Vacuum Sealing for Treatment of Problematical Wounds.).

Fleischmann, Vacuum sealing: indication, technique, and results, European Journal of Orthopaedic Surgery & Traumatology (1995).

Flynn, M.E. and D.T. Rovee, Wound Healing Mechanisms, *Amer. Journ. Of Nursing*, Oct. 1982, 1544-1556.

Fox, J.W. and G.T. Golden, The Use of Drains in Subcutaneous Surgical Procedures, *Amer. Journ. Of Surg*, Nov. 1976, 132, 673-674.

Garcia-Rinaldi, R., et al., Improving the Efficiency of Wound Drainage Catheters, Amer. Journ. Of Surg., Sep. 1975, 130, 372-373.

Gill, P., What is a Counter-Irritant? Name Three and the Method of Applying them, *Brit. Journ. Nurs.*, Jun. 1934, 142.

Goddard, L., Inflammation: Its Cause and Treatment, *Brit. Journ. Nurs.*, Jan. 1944, 2.

Gogia, Prem P., "The Biology of Wound Healing." Ostomy/ Wound Management. Nov.-Dec. 1992, pp. 12-20.

Gouttefangeas, C. et al., Functional T Lymphocytes Infiltrate Implanted Polyvinyl Alcohol Foams During Surgical Wound Closure Therapy, *Clin. Exp. Immunol. 2001*, 124, 398-405.

Grishdevich, V. and N. Ostrovsky, Postburn Facial Resurfacing with a Split Ascending Neck Flap, *Plastic and Reconstructive Surgery*, Dec. 1993, 1384-1391.

Grobmyer, et al., High-Pressure Gradients Generated by Closed-Suction Surgical Drainage Systems, *Surg. Infect. (Larchmt), Autumn 2002*, 3(3), 245-249, *Abs.*, Downloaded Nov. 30, 2003.

Grover, R. and R. Sanders, Recent Advances: Plastic Surgery, Clinical Review, *BMJ*, Aug. 8, 1998, 317, 397-400.

Gwan-Nulla, D.N. and R.S. Casal, Toxic Shock Syndrome Associated with the Use of the Vacuum-Assisted Closure Device, *Ann. Plast. Surg.*, Nov. 2001, 47(5), 552-554.

Hallstrom, B.R. and J.F. Steele, Postoperative Course after Total Hip Arthroplasty: Wound Drainage versus No Drainage, *Orthopaedic Review*, Jul. 1992, 847-851.

Hargens et al., Space Physiology Laboratory, Life Science Division, NASA Ames Research Center, "Control of Circulatory Functions in Altered Gravitational Fields.", Physiologist, Feb. 1992.

Hargens et al., Aviation, Space and Environmental medicine, pp. 934-937, Oct. 1991, "Lower Body Negative Pressure to Provide Load Bearing in Space."

Harkiss, K., Cheaper in the Long Run, *Community Outlook*, Aug. 1985, 19-22.

Hartz, R.S., et al., Healing of the Perineal Wound, *Arch. Surg.*, Apr. 1980, 115, 471-474.

Hay, J., et al., Management of the Pelvic Space With or Without Omentoplasty after Abdominoperineal Resection for Carcinoma of the Rectum: a Prospective Multicenter Study, *Eur. J. Surg*, 1997, *Abs*.

Hilsabeck, J.R., The Presacral Space as a Collector of Fluid Accumulations Following Rectal Anastomosis: Tolerance of Rectal Anastomosis to Closed Suction Pelvic Drainage, *Amer. Soc. Of Colon and Rectal Surgeons*, Oct., 25(7), 680-684, Oct. 1982.

Hilton, P., Surgical Wound Drainage: A Survey of Practices among Gynaecologists in the British Isles, *Br. Journ. Of Obstetrics and Gynaecology*, Oct. 1988, 95, 1063-1069.

Hollis, H.W. and M.R. Troy, A Practical Approach to Wound care in patients with Complex Enterocutaneous Fistulas, *Surg., Gyn. & Obs.*, Aug. 1985, 161, 179-181.

Hugh, T.B., Abdominal Wound Drainage, *Med. Journ. Of Australia*, May 4, 1987, 146, p. 505 (*Correspondence*).

Hulten, L., et al., Primary Closure of Perineal Wound after Proctocolectomy or Rectal Excision, *Acta Chir. Scand.*, 1971, 137, 467-469.

Hunt, T.K. and J.E. Dunphy, Eds., Fundamentals of Wound Management, *Appleton-Century-Crofts/New York*, 416-447, 1979.

Ilizarov, G.A., The Tension-Stress Effect on the Genesis and Growth of Tissues: Part II., *Clinical Orthopaedics and Related Research*, Feb. 1989, 239, 263-283.

Izmailov, S.G., et al., Device for Treatment of wounds and Abdominal Cavity, Contents, Surg. No. 8 1997, 1 page, Downloaded from internet http://www.mediasphera.ru/surgery/97/8/e8-97ref.htm.

Izmailov, S.G., The Treatment of Eventrations with a Special Apparatus, Abstracts, Surg. No. 1 1997, Downloaded from internet, 1 page, http://www.mediasphera.ru/surgery/97/1/el-97ref.htm.

Jeter, Katheerine F. Et, Managing Draining Wounds and Fistulae: New and Established Methods, Chronic Wound Care, Chapter 27, pp. 240-246, 1990.

Johnson, F.E., An Improved Technique for Skin Graft Placement using a Suction Drain, *Surgery, Gynecology & Obstetrics*, Dec. 1984, 159(6), 584-585.

Kazan Medical Institute Doctors, A Gadget to Bring the Wound Edges Close, 78-79 (in Russian with English translation). Aug. 20, 1985.

KCI, Inc., The V.A.C. System, 2000-2001, Brochure, 2 pgs.

Keen, W.W., Ed., Surgery, Its Principles and Practice, 1919, W. B. Saunders Company, p. 56, excerpt.

Keith, C.F., Wound management Following Head and Neck Surgery, *Nursing Clinics of North America*, Dec. 1979, 14(4) 761-779.

Kennard, H.W., Bier's Hyperaemia, *Brit. Journ. Nurs.*, Mar. 20, 1909, 223.

Khil'Kin, A.M., Use of a Collagen Hemostatic Sponge for the Experimental Closing of the Surface of a Liver Wound (article in Russian), Citation Downloaded from internet http://www.ncbi.nlm.nih.gov Apr. 24, 2006.

Kim, S.H., et al., Wangensteen Suction Drainage, apparatus in Neurosurgical Practice, *Dept. of Neurosurgery, Yonsei University of College of Medicine*, Seoul, Korea, 1975, 159-160, *Abs.* (*in Korean and Abstract in English*).

Klemp et al., The Journal of Investigative Dermatology, pp. 725-726 (1989), "Subcutaneous Blood Flow in Early male pattern Baldness."

Kloth, L.C. and J.M. McCulloch, Wound Healing Alternatives in Management, 3$^{rd}$ Ed., Chap. 10, 339-352, 2002.

Kohlman, Phyllis A., et al, "Pouching Procedure to Collect Drainage From Around a Biliary Drainage Catheter," Ostomy/Wound Management, Nov./Dec. 1991, pp. 47-50, vol. 37.

Landes, R.R. and I. Melnick, An Improved Suction Device for Draining Wounds, *Arch. Surg.*, May 1972, 104, p. 707.

Letsou et al. "Stimulation of Adenylate Cyclase Activity in Cultured Endothelial Cells Subjected to Cyclic Stretch." Cardiovascular Surgery 3. Toronto. Sep. 1989, pp. 634-639.

Linden van der, Willem, Randomized Trial of Drainage After Cholecystectomy, Modern Operative Techniques, Voluje 141, Feb. 1981, pp. 289-294.

Lockwood, C.B., Aseptic Surgery, Drainage, *Brit. Journ. Nurs.*, Mar. 26, 1904, p. 245.

Lumley, J.S.P., et al., The Physical and bacteriological Properties of Disposable and Non-Disposable Suction Drainage Units in the Laboratory, *Br. J. Surg.*, 1974, 61, 832-837.

Lundvall, J. and T. Lanne, Transmission of Externally applied Negative pressure to the Underlying Tissue: A Study on the Upper Arm of Man, *Acta Physiol. Scand.* 1989, 136, 403-409.

M. Gosta Arturson, *The Pathophysiology of Severe Thermal Injury*, JBCR, 6(2): 129-146 (Mar.-Apr. 1985).

Maddin et al., International Journal of Dermatology, 29: 446-450 (1990), "The Biological Effects of a Pulsed Electrostatic Field with Specific References to Hair: Electrotrichogenesis."

Magee, C., et al., Potentiation of Wound Infection by Surgical Drains, *Amer. Journ. Of Surg.*, May 1976, 131, pp. 547-549.

Maitland and Mathieson, Suction Drainage, *Brit. J. Surg,*, Mar. 1970, 57(3), pp. 195-197.

Mayo, C.W., The One-Stage Combined Abdominoperineal Resection for Carcinoma of the Rectum, RectoSigmoid and Sigmoid, *Surgical Clinics of North America*, Aug. 1939, *Mayo Clinic Number*, pp. 1011-1012.

McFarlane, R.M., The Use of Continuous Suction under Skin Flaps, *Br. Journ. Plast. Surg.*, pp. 77-86, 1958.

McGuire, S., Drainage after Abdominal Section, *Br. Journ. Of Nurs.*, Dec. 15, 1903, pp. 447-449.

McLaughlan, James, Sterile Microenvironment For Postoperative Wound Care, The Lancet, pp. 503-504, Sep. 2, 1978.

Medela, Inc., Pleupump MK II, Aug. 14, 2001, Brochure (in German), 12 pages.

Mendez-Eastman, S., Guidelines for Using Negative Pressure Wound Therapy, *Advances in Skin & Wound Care*, 14(6), Nov./Dec. 2001, pp. 314-325.

Mendez-Eastman, S., When Wounds Won't Heal, *RN*, Jan. 1998, pp. 2-7.

Meyer and Schmieden, Bier's Hyperemic Treatment, Fig. 69-70, 1908, p. 557.

Meyer, W. and V. Schmieden, Bier's Hyperemic Treatment, Published 1908 W. B. Saunders Company. (the entire reference has been submitted, but pp. 44-65 may be the most relevant).

Miles, W. Ernest, "Technique of the Radical Operation for Cancer of the Rectum", The British Journal of Surgery,pp. 292-304, United Kingdom 1914-1915.

Miles, W.E., A Method of Performing Abdominoperineal Excision for Carcinoma of the Rectum and of the Terminal Portion of the Pelvic Colon, *The Lancet*, Dec. 19, 1908, 1812-1813.

Milsom, I. and A. Gustafsson, An Evaluation of a Post-Operative Vacuum Drainage System, *Curr. Med. Res. Opin.* (1979), 6, 160-164.

Moloney, G.E., Apposition and Drainage of Large Skin Flaps by Suction, *Australian and New Zealand Journ. Of Surg.*, 173-179—1950's.

Morykwas, M.J., et al., Effects of Varying Levels of Subatmospheric Pressure on the Rate of Granulation Tissue Formation in Experimental Wounds in Swine, *Abs., Ann. Plast. Surg. 2001*, 47: 547.

Moserova, J. and E. Houskova, The Healing and Treatment of Skin Defects, 1989, 116-143.

Moss, W., What is Cellulitis? Describe Some Forms of Treatment You Would Expect to be Used for Cellulitis of the Arm, *Brit. Journ. Nurs.*, Nov. 1935, 282.

Mulder, G.D., Ed., et al., Clinicians' Pocket Guide to Chronic Wound Repair, *Wound Healing Publications*, Spartanburg, SC, 1991, 54-55.

Mullner, T., et al., The Use of Negative Pressue to Promote the Healing of Tissue Defects: A Clinical Trial Using the Vacuum Sealing Technique, *Br. J. Plast. Surg.*, Apr. 1997, 51(1), 79, *Abs*.

Musashaikhov, K.T., et al., The Course of Wound Healing under the Influence of Polyphepan in patients with Diabetes Mellitus, Abstracts, Surg. No. 5, 1997, Downloaded from internet, http://www.mediasphera.ru/surgery/97/5/e5-97ref.htm.

Nakayama, Yoshio, et al., A New Method for Dressing of Free Skin Grafts, New Method for Free Skin Grafting, vol. 86, No. 6 Jun. 12, 1989.

Nakayama, Y., et al., "A New Method for the Dressing of Free Skin Grafts", Plastic and Reconstructive Surgery, Dec. 1990 pp. 1216-1219, UK.

Nakayama et al., Ann. Plast. Surg., 26: 499-502 (1991), "A New Dressing Method for Free Skin Grafting in Hands."

Nasser, A.N., The Use of the Mini-Flap Wound Suction Drain in maxillofacial Surgery, *Annals of the Royal College of Surgeons of England*, 1986, 68, 151-153.

Navsaria, P.H., et al., Temporary Closure of Open Abdominal Wounds by the Modified Sandwich-Vacuum Pack Technique, *Br. Journ. Surg.*, 2003, 90, 718-722.

Nghiem, D.D., A Technique of Catheter insertion for Uncomplicated Peritoneal Dialysis, *Surgery, Gynecology & Obstetrics*, Dec. 1983, 157, 575-576.

Nicholas, J.M., Options for Management of the Open Abdomen, Presentation from Emory University School of Medicine, 66 pgs, Boston, MA, Apr. 26, 2004.

Nightingale, K., Making Sense of Wound Drainage, *Nursing time* Jul. 5, 1989, 85(27), 40-42.

Noblett, E.A., What is an Empyema? What Operations are Undertaken for its Relief, and What Have You to Say About the After-Nursing?, *Brit. Journ. Nurs.*, Apr. 29, 1916, 375.

O'Byrne, C., Clinical Detection and Management of Postoperative Wound Sepsis, *Nursing Clinics of North American*, Dec. 1979, 14(4), 727-741.

Ohotskii, V.P., et al., Usage of Vacuum Suction During the Primary Surgical Debridement of Open Limb Injuries, *Sovetskaya Medicina*, Jan. 17-20, 1973, (in Russian with English translation).

Olenius et al., "Mitotic Activity in Expanded Human Skin." Plastic and Reconstructive Surgery. Feb. 1993. 213-215.

Orgill, D., et al., Current Concepts and Approaches to Wound Healing, *Critical Care Medicine*, Sep. 1988, 16(9), 899-908.

Oschsner, A.J., Surgical Diagnosis and Treatment, 1921, 11, 266-269.

Parulkar, B.G., et al., Dextranomer Dressing in the Treatment of Infected Wounds and Cutaneous Ulcers, *J. Postgrad. Med.*, 1985, 31(1), 28-33.

Penman, M., What Are the Signs and Symptoms of Gallstones? What Instruments Would You have Ready for the Operation? How Would You Nurse a Case After Operation?, *Brit. Journ. Nurs.*, Aug. 9, 1919, 88.

Precision Medical, Power VAC+ Intermittent Aspirator, http://precisionmedical.com Downloaded from internet Apr. 10, 2006.

Putney F. Johnson, "The Use of Continuous Negative Pressure after Laryngectomy and Radical Neck Dissection", Surgery, Gynecology & Obstetrics, Aug. 1956, pp. 244-246, USA.

R.A.F. Clark et al., The Molecular and Cellular Biology of Wound Repair, Chapter 1 (1988).

Ramirez, O.M., et al., Optimal Wound Healing under Op-Site Dressing, Ideas and Innovations, 73(3), 474-475. May 9, 1983.

Ranson, John H. M.D., Safer Intraperitoneal Sump Drainage, Surgery Gynnecology and Obstetrics, pp. 841-842, 1973 vol. 137.

Redon, H. and J. Troques, La Fermeture Sous Depression des Plaies Etendues, *Academe de Chirurgie*, Mar. 1954, 304-306. (in French).

Reimann, D., et al., Successful Treatment Due to Vacuum Seal Technique of a Severe Scedosporium Apiospermum Skin Infection in a Renal Transplant Recipient, *Nephrol. Dial. Transplant*, 2004, 19 (1), 245-248.

Richter, Treatment of Inflammatory Conditions of the Skin with Hot Baths, *Brit. Journ. Nurs.*, Aug. 25, 1906, 149.

Roberts, R.H., et al., Randomised Trial of Medinorm LVS and Surgivac Drainage System after Operations for Breast Cancer May 1999, *Amer. Journ. Surg.*, Feb. 1997, 2 pgs.

Rosser, C.J., et al., A New Technique to Manage Perineal Wounds, *Infections in Urology*, Mar./Apr. 2000, 4 pgs.

Royle, G.T. and B.J. Britton, Disposable Drains, *Articles of the Royal College of Surgeons of England*, (1984), vol. 66, 1 page.

Russ and Fleischmann, Vakuumversiegelung, List of References (in English and German), 2000, 4 pgs.

Sagi, A., Burn Hazard from Cupping—An Ancient Universal Medication Still in Practice, *burns*, 1988, 14(4), 323-325.

Sames, C.P., Sealing of Wounds with Vacuum Drainage, *Br. Med. Journ.*, Nov. 5, 1977, p. 1223, *Correspondence*.

Sandahl, L., Slides at Geisinger Medical Center, Danville, PA, Apr. 10, 1990, Correspondence.

Schaffer, D.B., Closed Suction Wound Drainage, Nursing97, Nov., Downloaded from internet www.springnet.com, 62-64. 1997.

Schumann, D., Preoperative Measures to Promote Wound Healing, *Nursing Clinics of North America*, Dec. 1979, 14(4), 683-699.

Scott, F., Babies in Bottles, *Advance for Resp. Care Practitioners*, Nov. 23, 1992, 2 pgs.

Senyutovich, R.V., Napkin Preventing Abdominal Contamination in Performance of Colonic Anastomosis, Abstracts, Downloaded from internet, http://www.mediasphera.ru/ surgery/97/1/el-97ref.htm—1997.

Shaer, W.D., et al., Inexpensive Vacuum-Assisted Closure Employing a Conventional Disposable Closed-Suction Drainage System, *Plastic and Reconstructive Surgery*, Jan. 2001, 292.

Sheen, A.W., Some Experiences of Shell Wounds in the Present War, (excerpt), *Brit. Journ. Nurs.*, Jan. 16, 1915, 42.

Sheppard, M.D., "Sealed Drainage of Wounds", The Lancet, Jun. 14, 1952, pp. 1174-1176.

Smith, L.A., et al., Vacuum Pack Technique of Temporary Abdominal Closure: A Four-Year Experience, *Amer. Surg.*, Dec. 1997, 63(12), 1102-1108.

Spahn, Slide presented at the WOCN meeting in Ontario, California, Sep. 2001.

Spengler, Michael D., el al, "Performance of Filtered Sump Wound Drainage Tubes", Surgery, Gynecology & Obstetrics, Mar. 1982, pp. 333-336, vol. 54, USA.

Stewart, M. F., et al., Cleaning v Healing, *Community Outlook*, Aug. 1985, 22-26.

Svedman, P., A Dressing Allowing Continuous Treatment of a Biosurface, *IRCS Med. Science: Biomed. Tech.; Clinic. Med.; Surg. And Transplantation*, 1979, 7, p. 221.

Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.

Swanson, L., Solving Stubborn-Wound problem Could Save Millions, Team Says, *JAMC*, 23 FEVR, 1999: 160(4), p. 556.

Taylor, Virginia, "Meeting the Challenge of Fistulas & Draining Wounds", Nursing, Jun. 1980, pp. 45-51, USA.

Tenta, L.T., et al., Suction Drainage of Wounds of the Head and Neck, *Surg. Gyn. & Ob.*, Dec. 1989, 169, p. 558.

Tittel, K. and G. Tolksdorff, Forum: VariDyne—Neue Standard in der Postoperative Wunddrainage (New Standards in Postoperative Wound Drainage), *Unfallchirurgie*, 1988 14(2), 104-107 (*in German with English Translation*).

Tribble, David E. M.D., An Improved Sump Drain-Irrigation Device of Simple Construction, Archives of Surgery New York, pp. 511-513, 1972 vol. 105.

Urschel, J.D., et al., The Effect of Mechanical Stress on Soft and Hard Tissue Repair; A Review, *Br. Journ. Plast. Surg.*, 1988, 41, 182-186.

U.S. Appl. No. 11/491,578, filed Jul. 24, 2006, Title: Negative Pressure Protection System.

U.S. Appl. No. 11/654,926, filed Jan. 17, 2007, Title: Container and Cover System.

U.S. Appl. No. 11/784,021, filed Apr. 5, 2007, Title: Instructional Medical Treatment System.

Usypov, Y. N. And M.V. Ephfanov, Active Drainage of wounds, Dept. of Hospital Surgery, Army Medical Academy, Leningrad, *Vestnik Chirurgia 1987*, April Edition, 42-45 (in Russian with English translation).

Valenta, A.L., Using the Vacuum Dressing Alternative for Difficult Wounds, *AIN*, Apr. 1994, 44-45.

Van Heurn, L.W.E. and P.R.G. Brink, Prospective Randomized Trial of High versus Low Vacuum Drainage after Axillary Lymphadenectomy, *Br. Journ. Surg. 1995*, 82, 931-932.

Van Way III, C.W., Prevention of Suction-Induced Gastric mucosal damage in Dogs, *Critical Care Medicine*, Aug. 1987, 15(8), 774-777.

Varley, G.W. and S.A. Milner, Wound Drains in Proximal Femoral Fracture Surgery: A Randomized prospective Trial of 177 Patients, *J. R. Coll. Surg. Edinb.*, Dec. 1995, 40, 416-418.

Vijanto, J. and J. Raekallio, Local Hyperalimentation of Open Wounds, *Br. J. Surg.*, 1976, 63, 427-430.

Warren, J.C. and A.P. Gould, Ed., The International Text-Book of Surgery, 1902, 1, 70-79.

Waymck, J.P., et al., An Evaluation of Aquaphor Gauze Dressing in Burned children, *Abs*, Aug. 1986; 12(6):443-8.

Wayne, M.A., Cook Pneumothorax Catheter Set, Wayne Pneumothorax Catheter Set, *Cook Critical Care, Cook Incorporated 1997*, 3 pgs.

Westaby, S., Wound Care No. 11, *Nursing Times*, Jul. 21, 1982, 41-48.

Williams, et al., Survey of the Use of Suction Drains in head and Neck Surgery and Analysis of Their Biomechanical Properties, *J. Otolaryngol.*, Feb. 2003, 32(1), 16-22, *Abs. Downloaded from internet* Nov. 30, 2003.

Windows on Medical Technology, Vacuum-Assisted Wound Closure for Chronic and Acute Wounds, , *ECRI Health Technology Assessment Information Service*, Oct. 2000, 38, 1-21.

Witkowski, J.A. and Parish, L.C., Synthetic Dressings: Wound Healing in the '80s, *Hospital Therapy*, Nov. 1986, 75-84.

Wolthuis, Roger A., et al, "Physiological Effects of Locally Applied Reduced Pressure in Man," *Physiological Reviews*, Jul. 1974, pp. 566-595 vol. 54, No. 3, USA.

Wooding-Scott, Margaret, et.al, "No Wound is Too Big for Resourceful Nurses," RN, Dec. 1988, pp. 22-25, USA.

Worth, M.H. and H.W. Andersen, The Effectiveness of Bacterial Filtration in Vented Wound Drains, *Journ. Of Surg. Research*, 1979, 27, 405-407.

Wu, P., et al., In Vitro Assessment of Water Vapour Transmission of Synthetic Wound Dressings, *Biomaterials*, 1995, 16(3), 171-175.

Wu, W.S., et al. Vacuum therapy as an intermediate phase in wound closure: a clinical experience, Eur J Past Surg (2000) 23: 174-177.

Wysocki et al., "Wound Fluid form Chronic Leg Ulcers Contains Elevated Levels of Metalloproteinases MMP-2 and MMP-9." The Society for Investigative Dermatology, Inc. Jul. 1993. 64-68.

Yukhtin, V.I., et al., Surgical Treatment of Purulent Diseases of Soft tissues and Bones with the Use of Drainage-Bathing System, Content, Surg. No. 9 1997, Downloaded from internet, http://www.mediasphera.ru/surgery/97/9/e9-97ref.htm.

Zamierowski, David S., Letter:"All Foam Sponges are not Equal in Vacuum Dressings," British Journal of Plastic Surgery, 1999, 52, 78-81, p. 79, United Kingdom.

Zhetimkarimov, D.S. and V.K. Ostrovsky, The Applied Significance of Anatomic Pecularities of Greater Momentum, CONTENTS, Surg. No. 6, 1997, Downloaded from internet http://www.mediasphera.ru/surgery/97/6/e6-97ref.htm.

Chariker, M. E., et al, "Effective Management of Incisional and Cutaneous Fistulae with Closed Suction Wound Drainage," Contemporary Surgery, Jun. 1989, pp. 59-63, vol. 34, USA.

Wooding-Scott, Margaret, et al, "No Wound is Too Big for Resourceful Nurses," RN, Dec. 1988, pp. 22-25, USA.

Garcia-Renaldi, Raul, et al, "Improving the Efficiency of Wound Drainage Catheters," Journal of Surgery (?), Sep. 1975, pp. 372-373, vol. 130.

Schwab, Peter M. and Kelly, Keith A., "Primary closure of the Perineal Wound After Proctectomy," Mayo Clinic Proc., Mar. 1974, pp. 176-179, vol. 49, USA.

Ramirez, Oscar M., et al, "Optimal Wound Healing Under Op-Site Dressing," , pp. 474-475, vol. 73, No. 3, Ideas and Innovations, May 9, 1983.

Raffl, Arthur B., "Use of Negative Pressure Under Skin Flaps After Radical Mastectomy," Dept. of Surgery, State Univ. of N.Y., College of Medicine, Syracuse, NY, Submitted for publication Apr. 1953, p. 1048, USA.

Knight, Marie Ray, "A Second Skin for Patients with Large, Draining Wounds," Nursing, Jan. 1976, p. 37, USA.

Spengler, Michael D., et al, "Performance of Filtered Sump Wound Drainage Tubes", Surgery, Gynecology & Obstetrics, Mar. 1982, pp. 333-336, vol. 54, USA.

Alper, Joseph. C., "Recent Advances in Moist Wound Healing," Southern Medical Journal, Nov. 1988, pp. 1398-1404, vol. 79, No. 11, USA.

Davydov, Yu. A., et al, Article in Russian (?): Abstract in English: "Vacuum Therapy in the Treatment of Purulent Lactation Mastitis", pp. 66-70, Vestnik Chirurgia 1986, September Edition (In Russian with English translation).

Davydov, Yu. A., et al, Article in Russian (?): Abstract in English: "The Bacteriological and Cytological Assessment of Vacuum Therapy of Purulent Wounds", pp. 48-52, Vestnik Chirurgia 1987, October Edition.

Putney, F. Johnson, "The Use of Continuous Negative Pressure after Laryngectomy and Radical Neck Dissection", Surgery, Gynecology & Obstetrics, Aug. 1956, pp. 244-246, USA.

Brummelkamp, W.H., et-al, "High-vacuum drainage and primary perineal wound closure in abdominoperineal excision of the rectum", The Netherlands Journal of Surgery, 1991 pp. 236-238, Netherlands.

Unknown, "Wound Suction", Nursing, Oct. 1975, pp. 52-53, USA.

Zamierowski, David S., Letter: "All Foam Sponges are not Equal in Vacuum Dressings," British Journal of Plastic Surgery, 1999, 52, 78-81, p. 79, United Kingdom.

Unknown, "The RN Magazine/University of California Continuing Education Curriculum; Examination on 'To heal a draining wound'", RN, Mar. 1982, p. 36, USA.

* cited by examiner

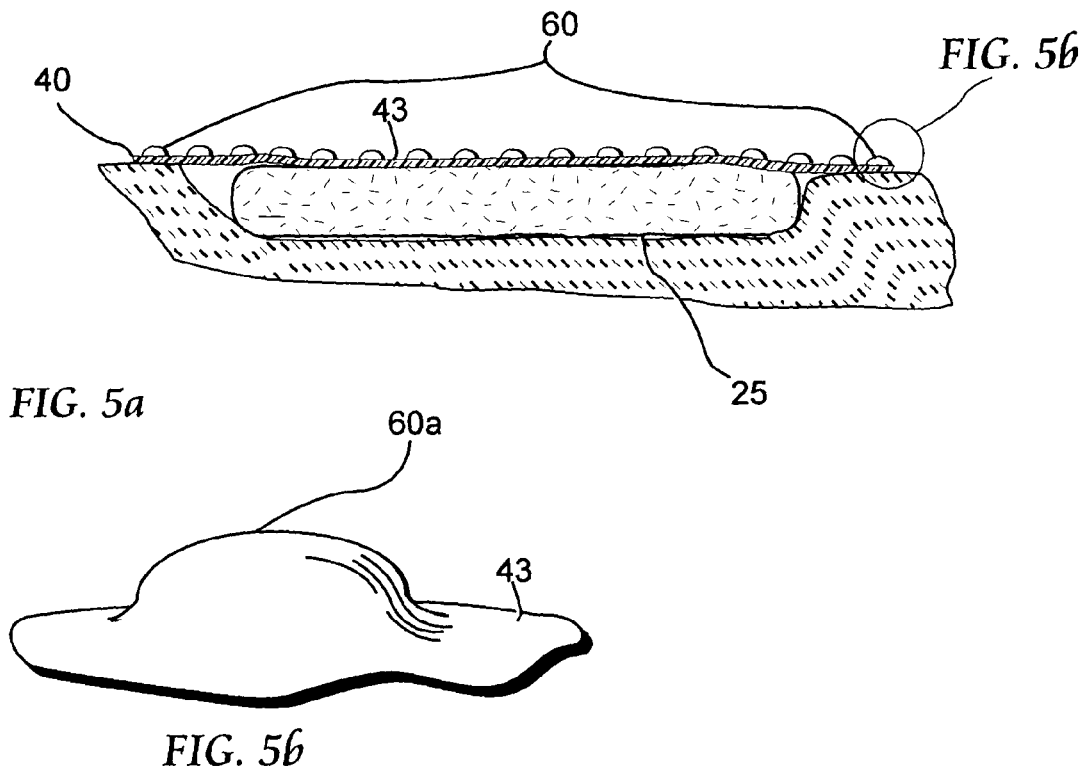
FIG. 5a
FIG. 5b
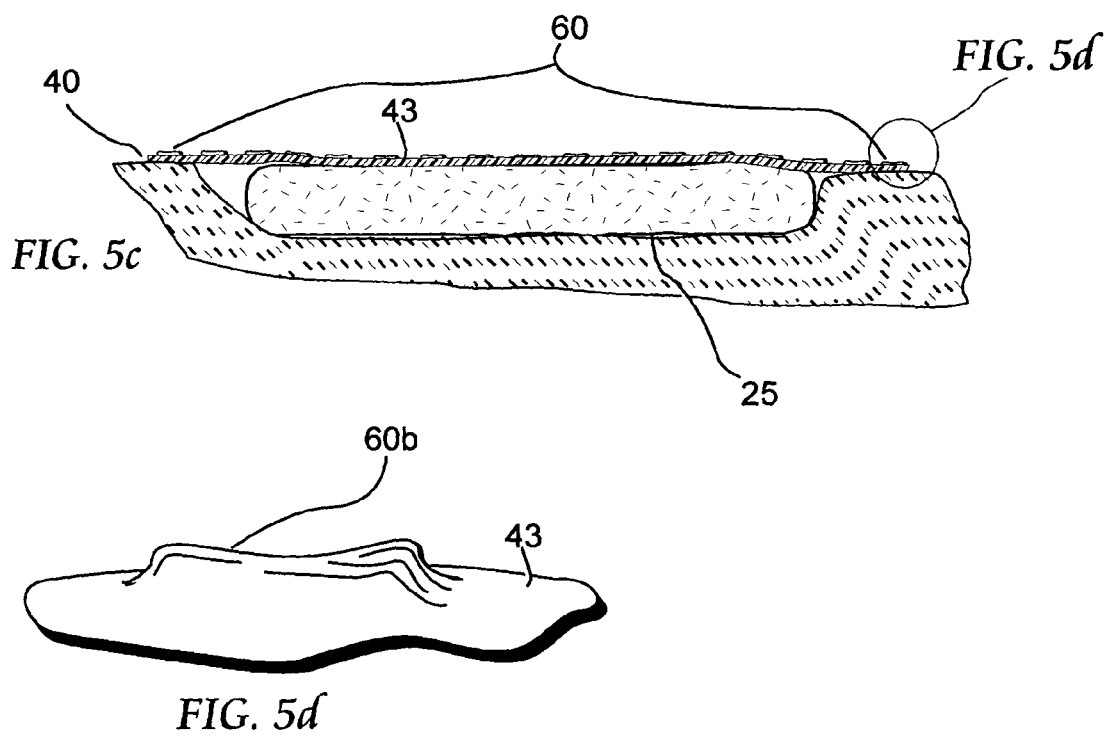
FIG. 5c
FIG. 5d

REDUCED PRESSURE TREATMENT SYSTEM

CROSS REFERENCES TO OTHER APPLICATIONS

This application claims the benefit of U.S. provisional application No. 60/407,783, filed on Sep. 3, 2002, and U.S. provisional application No. 60/430,827, filed on Dec. 4, 2002. The full disclosures of both provisional applications are incorporated herein by reference.

BACKGROUND

The present invention relates to an apparatus and a method for treating a wound by applying reduced pressure to the wound. In this context, the term "wound" is to be interpreted broadly, to include any body part of a patient that may be treated using reduced pressure.

The treatment of open or chronic wounds that are too large to spontaneously close or otherwise fail to heal has long been a troublesome area of medical practice. Closure of an open wound requires inward migration of surrounding epithelial and subcutaneous tissue. Some wounds, however, are sufficiently large or infected that they are unable to heal spontaneously. In such instances, a zone of stasis in which localized edema restricts the flow of blood to the epithelial and subcutaneous tissue forms near the surface of the wound. Without sufficient blood flow, the wound is unable to successfully fight bacterial infection and is accordingly unable to close spontaneously.

An initial stage of wound healing is characterized by the formation of granulation tissue which is a matrix of collagen, fibronectin, and hyaluronic acid carrying macrophages, fibroblasts, and neovasculature that forms the basis for subsequent epithelialization of the wound. Infection and poor vascularization hinder the formation of granulation tissue within wounded tissue, thereby inhibiting wound healing. It therefore becomes desirable to provide a technique for increasing blood circulation within wounded tissue to promote spontaneous healing and to reduce infection.

Another problem encountered during the treatment of wounds is the selection of an appropriate technique for wound closure during the healing process. Sutures are often used to apply force to adjacent viable tissue in order to induce the edges of a wound to migrate together and heal. However, sutures apply a closure force to only a very small percentage of the area surrounding a wound. When there is scarring, edema, or insufficient tissue, the tension produced by the sutures can become great causing excessive pressure to be exerted by the sutures upon the tissue adjacent to each suture. As a result, the adjacent tissue often becomes ischemic thereby rendering suturing of large wounds counterproductive. If the quantity or size of the sutures is increased to reduce the tension required of any single suture, the quantity of foreign material within the wound is concomitantly increased and the wound is more apt to become infected. Additionally, the size or type of a particular wound may prevent the use of sutures to promote wound closure. It therefore becomes desirable to provide an apparatus and method for closing a large wound that distributes a closure force evenly about the periphery of the wound.

Wounds resulting from ischemia, or lack of blood flow, are also often difficult to heal since decreased blood flow to a wound may inhibit normal immune reaction to fight infection. Patients that are bedridden or otherwise non-ambulatory are susceptible to such ischemic wounds as decubitus ulcers or pressure sores. Decubitus ulcers form as a result of constant compression of the skin surface and underlying tissue thus restricting circulation. Since the patient is often unable to feel the wound or to move sufficiently to relieve the pressure, such wounds can become self-perpetuating. Although it is common to treat such wounds with flaps, the conditions that initially caused the wound may also work against successful flap attachment. Wheelchair-bound paraplegics, for example, must still remain seated after treatment of pelvic pressure sores. It therefore becomes desirable to provide a treatment procedure for ischemic wounds that can be conducted in situ upon an immobile or partially mobile patient.

Other types of wounds in which ischemia leads to progressive deterioration include partial thickness burns. A partial thickness burn is a burn in which the cell death due to thermal trauma does not extend below the deepest epidermal structures such as hair follicles, sweat glands, or sebaceous glands. The progression of partial thickness burns to deeper burns is a major problem in burn therapy. The ability to control or diminish the depth of burns greatly enhances the prognosis for burn patients and decreases morbidity resulting from burns. Partial thickness burns are formed of a zone of coagulation, which encompasses tissue killed by thermal injury, and a zone of stasis. The zone of stasis is a layer of tissue immediately beneath the zone of coagulation. Cells within the zone of stasis are viable, but the blood flow is static because of collapse of vascular structures due to localized edema. Unless blood flow is re-established within the zone of stasis soon after injury, the tissue within the zone of stasis also dies. The death of tissue within the zone of stasis is caused by lack of oxygen and nutrients, reperfusion injury (re-establishment of blood flow after prolonged ischemia), and decreased migration of white blood cells to the zone resulting in bacterial proliferation. Again, it becomes desirable to provide a technique for treating burn wounds by enhancing blood circulation to the wounded tissue to inhibit burn penetration.

There exist various apparatus utilizing reduced pressure for treatment of these types of wounds. See, for example, U.S. Pat. No. 5,636,643. The apparatus existing in the art is generally comprised of a fluid impermeable cover that covers the wound, which is directly or indirectly connected to a source of suction so that an area of reduced pressure is created beneath the cover in the area of the wound. Some type of packing material, such as gauze, is also often placed in the area of the wound beneath the cover to prevent overgrowth of the wound. Apparatus existing in the relevant art, however, suffer from several disadvantages.

One such disadvantage is the necessity to change the packing material placed in the wound during the period of treatment. This requirement is expensive because multiple dressings are necessary and medical staff must expend time to change the dressings. In addition, there is an increased risk of infection and intrusion of other harmful foreign material into the wound area. It is therefore desirable to have a reduced pressure wound treatment system having a dressing that does not need to be changed, or needs to be changed fewer times, during the period of treatment.

In addition, the existing apparatus do not have adequate means to monitor the pressure in the area of the wound beneath the cover. If the cover is not adequately sealed to the tissue surrounding the wound, reduced pressure cannot be maintained beneath the cover so that the benefits of the treatment are lost or diminished. In addition, pressure leaks through the seal cause the source of suction to operate more frequently, which consumes more energy and causes the suction equipment to wear faster than it would otherwise, reducing its useful life. Further, the flow of air into the wound area as a result of such leaks can result in increased risk of infection and intrusion of other harmful foreign material into the wound area. It is therefore desirable to have a relatively inexpensive means of monitoring the pressure level beneath the cover at the site of the wound.

In addition, the existing apparatus do not have a means to determine the amount of blood flow to the tissue at the site of the wound. As discussed above, adequate blood circulation in the area of the wound is essential for the healing process to proceed as desired. Areas of tissue having an increased level of blood circulation generally have a higher temperature than areas that have a comparatively lower level of blood circulation. It is therefore desirable to have a means of monitoring the relative temperature within the area of the wound.

Finally, it is sometimes necessary to transport patients in need of reduced pressure wound care. It is also sometimes necessary to provide reduced pressure treatment in the field. It is therefore also desirable to have a wound treatment apparatus that is portable and self-contained, which can accompany the patient during such transport or be used to provide reduced pressure treatment in the field.

SUMMARY

The present invention is directed to a reduced pressure wound treatment apparatus and method that satisfy the needs described above. As described in greater detail below, it has many advantages over existing apparatus when used for its intended purpose, as well as novel features that result in a new reduced pressure wound treatment apparatus and method that are not anticipated, rendered obvious, suggested, or even implied by any of the prior art apparatuses, either alone or in any combination thereof.

In accordance with the present invention a wound treatment apparatus is provided for treating a wound by applying reduced pressure (i.e. pressure that is below ambient atmospheric pressure) to the wound in a controlled manner for a selected time period in a manner that overcomes the disadvantages of currently existing apparatus. The application of reduced pressure to a wound provides such benefits as faster healing, increased formation of granulation tissue, closure of chronic open wounds, reduction of bacterial density within wounds, inhibition of burn penetration, and enhancement of flap and graft attachment. Wounds that have exhibited positive response to treatment by the application of negative pressure include infected open wounds, decubitus ulcers, dehisced incisions, partial thickness burns, and various lesions to which flaps or grafts have been attached.

The wound treatment apparatus in accordance with the present invention includes a reduced pressure application appliance that is applied to a treatment site at which there is a wound and normal tissue surrounding the wound. The reduced pressure application appliance includes a fluid impermeable wound cover for covering and enclosing the wound. In a particular embodiment of the present invention, the wound cover also includes means for visually monitoring the pressure in the area of the site of the wound beneath the wound cover. These means include a plurality of protrusions on the surface of the cover that are recessed when a predetermined pressure is present beneath the cover, but are increasingly displaced above the remaining surface of the cover as the pressure beneath the cover increases above a predetermined pressure. In a similar manner, the cover may contain areas that are displaced as protrusions away from the remaining surface of the cover toward the wound when reduced pressure is applied beneath the cover, and the displacement of the protrusions decreases as the pressure beneath the cover increases. The protrusions may also be a different color (or a different shade of the same color) from that on the remaining surface of the cover. In addition, the protrusions may produce a noise as they are displaced away from the remaining surface of the cover, providing an audible indication that the pressure beneath the cover is increasing.

The appliance also includes sealing means for sealing the wound cover to the surrounding tissue of the wound in order to maintain reduced pressure in the vicinity of the wound during wound treatment. When the wound cover is sealed in position over the wound site, a generally fluid-tight or gas-tight sealed enclosure is formed over the wound site. The sealing means may be in the form of an adhesive applied to the underside of the wound cover for sealing the wound cover around the periphery of the wound. The sealing means may also include a separate sealing member such as an adhesive strip or a sealing ring in the form of a tubular pad or inflatable cuff secured to the wound cover for positioning around the periphery of the wound. In selected embodiments, the reduced pressure within the sealed enclosure under the wound cover may serve to seal the wound cover in position at the wound site. The reduced pressure appliance also includes a suction port for supplying reduced pressure within the sealed volume enclosed beneath the wound cover. The suction port may be in the form of a nipple on the wound cover. Alternatively, the suction port may be in the form of a tube attached to the wound cover or provided as a feedthrough beneath the wound cover.

The appliance may also include an absorbable matrix for placement in the wound in order to encourage tissue in the area of the wound to grow into the matrix during treatment. The absorbable matrix is constructed of an absorbable material that is absorbed into the epithelial and subcutaneous tissue in the wound as the wound heals. The matrix may vary in thickness and rigidity, and it may be desirable to use a spongy absorbable material for the patient's comfort if the patient must lie upon the appliance during treatment. The matrix may also be perforated and constructed in a sponge-type or foam-type structure to enhance gas flow and to reduce the weight of the matrix. Because of the absorbable nature of the absorbable matrix, the matrix should require less frequent changing than other dressing types during the treatment process. In other circumstances, the matrix may not need to be changed at all during the treatment process.

A vacuum system is connected with the reduced pressure appliance in order to provide suction or reduced pressure to the appliance. For this purpose, the vacuum system includes a suction pump or suction device for connection with the suction port of the appliance for producing the reduced pressure over the wound site. The vacuum system may include a section of hose or tube, such as a vacuum hose, that interconnects the suction device with the suction port of the appliance to provide the reduced pressure at the wound site. A fluid collection system may be provided intermediate the vacuum hose of the suction device and the suction port of the appliance to trap any exudate that may be aspirated from the wound by the negative pressure appliance. A stop mechanism may also be provided for the vacuum system to halt production of the reduced pressure at the wound site in the event that an excessive quantity of exudate has been collected. The apparatus may also include a control device for controlling the pump.

In a particular embodiment of the invention, the wound cover for the reduced pressure appliance may be in the form of a gas impermeable covering sheet of flexible polymer material such as polyethylene, having an adhesive backing that provides the seal for securing the sheet over the wound site to provide a gas-tight or fluid-tight sealed enclosure over the wound site. The vacuum system of the wound treatment apparatus may include a suction pump having a vacuum hose that is connected with a suction tube serving as a suction port for the appliance. The suction tube for the appliance runs beneath the cover sheet that is sealed in position over the wound site and into the fluid-tight enclosure provided under the cover sheet. An adhesive backing on the cover sheet is used to provide a fluid-tight seal around the feedthrough for the suction tube at the wound site. Within the enclosure, the suction tube is connected with the absorbable matrix for placement in the wound. The absorbable matrix functions to more uniformly apply reduced pressure or suction over the wound site while holding the cover sheet substantially out of the wound during the application of reduced pressure at the enclosed wound site.

In another particular version of the invention, the wound treatment apparatus also includes means to monitor the temperature of the tissue in the area of the wound. In a particular embodiment of this version of the invention, a temperature sensitive layer composed of a temperature sensitive material is placed adjacent to the lower surface of the wound cover. The temperature sensitive layer changes color, or changes from one shade of a color to another shade of the same color, as the temperature of the material changes. In this embodiment of the invention, the wound cover is composed of a transparent or semi-transparent material allowing the temperature sensitive material to be observed from above the wound cover. Alternatively, the wound cover is composed of a temperature sensitive material that changes color, or changes from one shade of a color to another shade of the same color, as the temperature of the material changes. In another embodiment of this version of the invention, one or more temperature measuring devices are placed in the area of the wound. The temperature measuring devices are preferably placed adjacent to the wound tissue, but may also be placed in other locations under or above the wound cover, to monitor the temperature of said tissue. Temperature measuring devices located under the wound cover have leads that feedthrough beneath the wound cover. The leads are connected to an alarm system that produces one or more alarm signals when the temperature measured by one or more of the temperature measuring devices exceeds or is lower than a predetermined value. In another embodiment of this version of the invention, the temperature measuring devices are also connected through their respective leads and the alarm system to a temperature display or recording device that produces a display or record of the temperature in the area of the wound.

In another particular version of the invention, the wound treatment apparatus is portable and self-contained. In this version of the invention, a miniature vacuum source is used to provide suction to the reduced pressure appliance. Similarly, the fluid collection system is of the minimum size desired to collect and maintain the amount of exudate expected to be aspirated from the wound during the time of anticipated use of the portable wound treatment apparatus. A filter may also be placed in the connection between the vacuum source and the fluid collection system to avoid contamination of the source by the fluid aspirated from the wound. As a result, reduced pressure treatment of a wound can continue even if it becomes necessary to transport the patient because the apparatus can accompany a patient during the transport. The portable apparatus is not, however, limited to this use alone. It can be used in any application where a portable treatment apparatus is advantageous, such as treatment of wounds in the field.

There has thus been outlined, rather broadly, the more primary features of the present invention. There are additional features that are also included in the various embodiments of the invention that are described hereinafter and that form the subject matter of the claims appended hereto. In this respect, it is to be understood that the invention is not limited in its application to the details of construction and to the arrangements of the components set forth in the following description or illustrated in the following drawings. This invention may be embodied in the form illustrated in the accompanying drawings, but the drawings are illustrative only and changes may be made in the specific construction illustrated and described within the scope of the appended claims. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The foregoing summary, as well as the following detailed description of the preferred embodiments of the present invention, will be better understood when read in conjunction with the appended drawings, in which:

FIG. 4b is a sectional elevational detailed view of the shutoff mechanism portion of the collection system of FIG. 4a;

FIG. 5a is a schematic sectional elevational view of a reduced pressure appliance in accordance with another embodiment of the present invention, shown in partial section, in which the reduced pressure appliance includes a flexible, fluid impermeable wound cover sealed over the wound, said cover having embedded within it protrusions that are displaced above the remaining surface of the cover;

FIG. 5b is a detailed perspective view of a protrusion from the reduced pressure appliance of FIG. 5a, in the fully displaced configuration;

FIG. 5c is a schematic sectional elevational view of the reduced pressure appliance of FIG. 5a, illustrating the cover having the protrusions in the depressed configuration when sufficient vacuum is present beneath the cover;

FIG. 5d is a detailed perspective view of a protrusion from the reduced pressure appliance of FIG. 5a, in the fully depressed configuration;

FIG. 8b is a sectional elevational detailed view of the shutoff mechanism portion of the collection system of FIG. 8a.

DETAILED DESCRIPTION OF THE PREFERRED EMBODIMENTS

Figure 1:
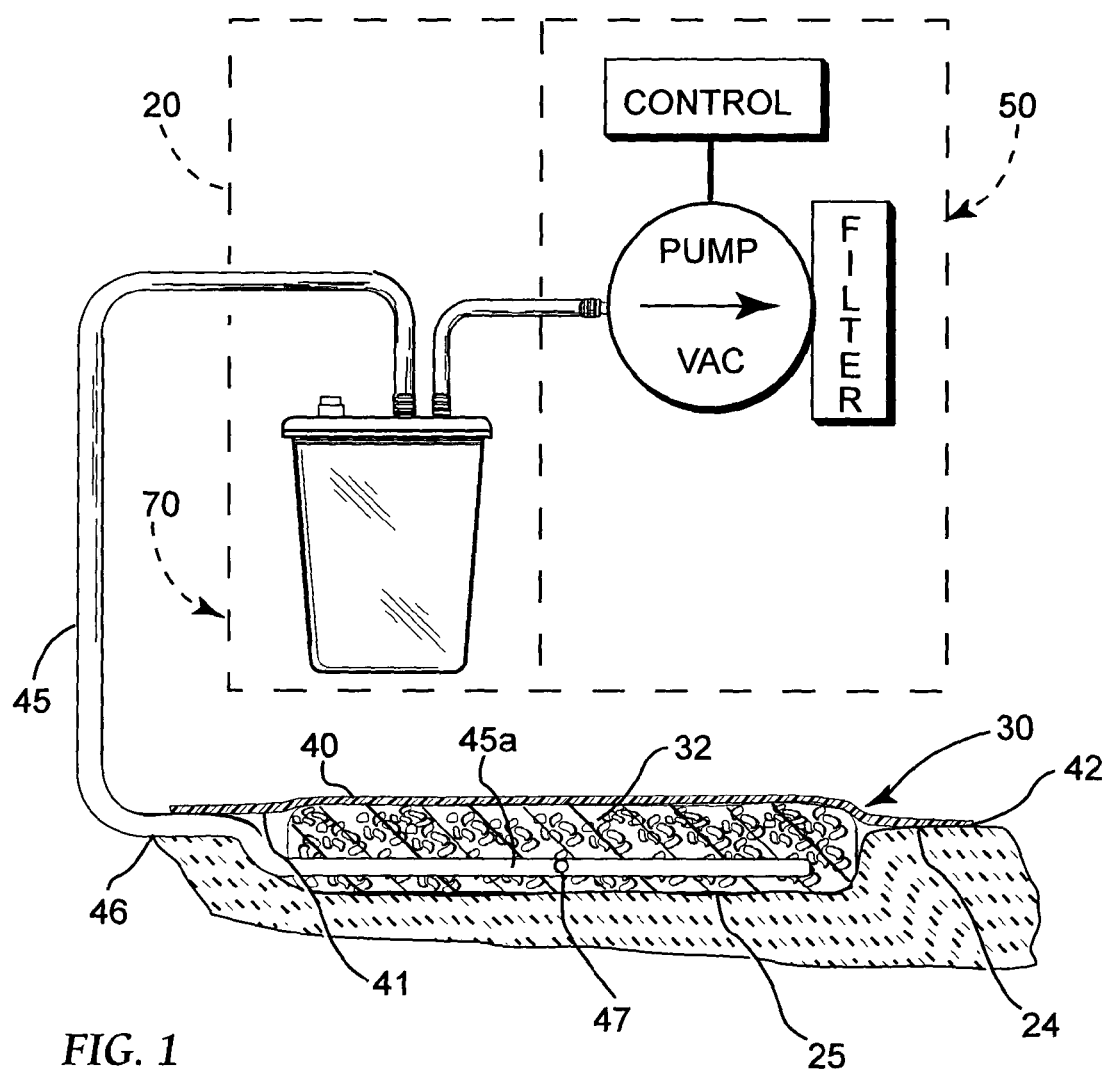
FIG. 1 is a schematic elevational view of a wound treatment apparatus in accordance with a particular embodiment of the present invention in which a reduced pressure appliance, shown in partial section, includes a flexible, fluid impermeable wound cover sealed over the wound and an absorbable matrix positioned in the wound, and in which a vacuum system provides reduced pressure within the wound cover of the appliance.

In accordance with the present invention, a wound treatment apparatus is provided for treating a wound by application of reduced pressure (i.e., below atmospheric pressure) so that suction may be applied to a wound site 25 in a controlled manner for a selected period of time. FIG. 1 schematically shows one version of the wound treatment apparatus, generally designated 20, which includes a reduced pressure appliance, generally designated 30, for enclosing a wound site 25 to provide a fluid-tight or gas-tight enclosure over the wound site 25 to effect treatment of a wound 25 with reduced or negative pressure. For the purpose of creating suction within the appliance 30, the appliance 30 is connected with a vacuum system, generally designated 50, to provide a source of suction or reduced pressure for the sealed appliance 30 at the wound site 25. Intermediate the appliance 30 and the vacuum system 50 is a fluid collection system, generally designated 70, for intercepting and retaining exudate that is aspirated from the wound site 25.

FIG. 1 also illustrates one embodiment of the reduced pressure appliance 30, which includes an absorbable matrix 32 that is placed within the wound 25, a fluid impermeable wound cover 40, and a suction port in the form of hollow tubing 45 that connects the appliance 30 to the vacuum system 50 (through the collection system 70) to provide reduced pressure in the area beneath the cover 40 in the area of the wound 25. FIG. 1 also illustrates one embodiment of an absorbable matrix 32, which is placed within the wound 25.

The absorbable matrix 32 is placed over substantially the expanse of the wound 25 to encourage growth of tissue in the area of the wound 25 into the matrix 32 as the wound heals. The size and configuration of the absorbable matrix 32 can be adjusted to fit the individual wound 25. It can be formed from a variety of absorbable materials, preferably a material that is also porous. The matrix 32 should be constructed in a manner so that it is sufficiently porous to allow oxygen to reach the wound 25. The absorbable matrix 32 is preferably constructed of a non-toxic material that is absorbable by the epithelial and subcutaneous tissue within the area of the wound 25, such as collogens derived from healthy mammals, absorbable synthetic polymers, or other materials similar to those used for absorbable dressings. An example is a dehydrating material derived from seaweed for treatment of exudating wounds. The matrix 32 may vary in thickness and rigidity, although it may be desirable to use a spongy or layered, non-woven absorbable material for the patient's comfort if the patient must lie upon the appliance 30 during treatment. The matrix 32 may also be perforated and constructed in a foam-type, sponge-type, or non-woven layered structure to enhance gas flow and to reduce the weight of the appliance 30. As shown in FIG. 1, the matrix 32 is cut to an appropriate shape and size to fit within the wound 25. Alternatively, the matrix 32 may be sufficiently large to overlap the surrounding skin 24. Further, the matrix 32 may be of uniform thickness over its entire area, as is the case where monitoring the temperature of tissue in the area of the wound is desired as a part of the treatment process.

Figure 2A:
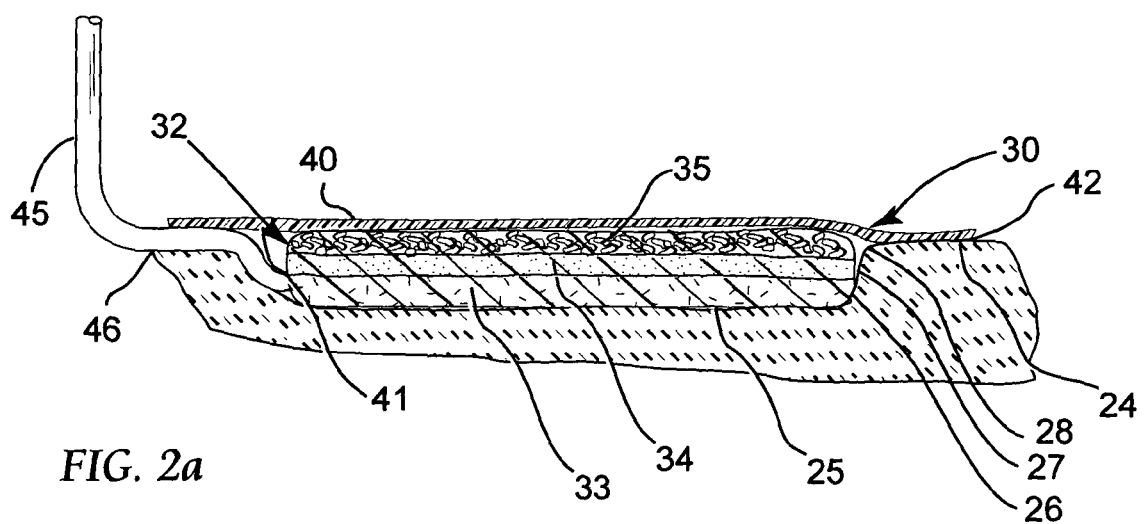
FIG. 2a is a schematic sectional elevational view of the reduced pressure appliance of FIG. 1, illustrating an absorbable matrix having three layers of absorbable material, such layers being of different absorbable materials.

In another embodiment of the invention, the absorbable matrix 32 has the same features as described above and as illustrated in FIG. 1, but may also be constructed of more than one absorbable material, such material having different rates of absorption into body tissue. By preselecting the materials of the matrix 32, and placing them in areas of the wound 25 in which different rates of absorption are desired, it may be possible to enhance wound healing. An example of this embodiment of the absorbable matrix 32 is illustrated in FIG. 2a, where the matrix 32 is composed of three layers, each layer being composed of an absorbable material different from the material in the adjacent layer. Thus, in a matrix 32 of three layers having the lowest layer 33 being constructed of an absorbable material, and the middle layer 34 of the matrix 32 being constructed of a material having a lower rate of absorption than the lowest layer 33, and the layer of the matrix 32 closest to the cover 40 (i.e., the highest layer 35) being constructed of a material having a rate of absorption lower than the other two layers, the area of the wound 25 adjacent to the lowest layer 26 would be allowed to close at a faster rate than the area of the wound 25 adjacent to the middle layer 27, and the area of the wound 25 adjacent to the highest layer 28 would be allowed to close at a faster rate than the area of the wound 25 adjacent to the middle layer 27 and the lowest layer 26. This embodiment of the invention is not limited to three layers or this gradation of absorption rates. Any combination of number of layers and absorbent materials desirable for wound treatment is possible and may be preferred. For example, the matrix 32 may have a highest layer 35 of absorbent material having a rate of absorption higher than the rate of absorption of the middle layer 34, which middle layer 34 has a higher rate of absorption than the rate of absorption of the lowest layer 33. Similarly, the highest layer 35 and the lowest layer 33 may have rates of absorption that are approximately equal to one another, such rate of absorption being greater or lesser than the rate of absorption of the middle layer 33.

Figure 2B:
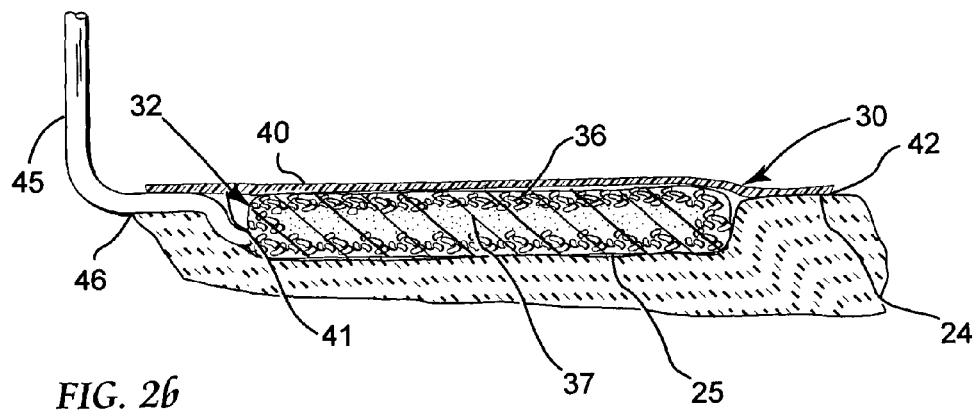
FIG. 2b is a schematic sectional elevational view of the reduced pressure appliance of FIG. 1, illustrating an absorbable matrix having generally concentric layers of absorbable material, such layers being of different absorbable materials.

In addition, this embodiment of the matrix 32 is not limited to layers. The matrix 32 may be constructed in any configuration having materials of different absorption rates in any portion of the matrix 32 that is desired to promote wound healing. For example, as illustrated in FIG. 2b, the material on the periphery 36 of the matrix 32 may be constructed of material having one rate of absorption, while the inner portions 37 of the matrix 32 may be constructed of one of more materials having different rates of absorption. This would allow for the wound 25 to close at one rate during the initial portion of the treatment period, and for the wound 25 to close at different rates during later portions of the treatment period. Other configurations that are possible include having approximately opposite sides or ends of the matrix 32 being constructed of a different material from the intermediate portions of the matrix 32.

The fluid-impermeable wound cover 40 in the embodiment of the reduced pressure appliance 30 illustrated in FIG. 1 is in the form of a flexible, adhesive, fluid impermeable polymer sheet for covering and enclosing the wound 25, including the absorbable matrix 32 within it, and the surrounding normal skin 24 at the wound site 25. The wound cover 40 includes an adhesive backing 41 which functions to seal the wound cover 40 to the normal skin 24 around the periphery of the wound 25 to provide a generally gas-tight or fluid-tight enclosure over the wound 25. The adhesive cover sheet 40 must have sufficient adhesion to form a fluid-tight or gas-tight seal 42 around the periphery of the wound 25 and to hold the sheet 40 in sealed contact with the skin 24 during the application of suction or reduced or negative pressure. The wound cover 40 also provides a gas-tight seal around the tubing 45 at the feedthrough location 46 where the tubing 45 emerges from beneath the wound cover 40. The wound cover 40 is preferably formed of a fluid impermeable or gas impermeable flexible adhesive sheet such as Ioban, a product of the 3M Corporation of Minneapolis, Minn.

Figure 3:
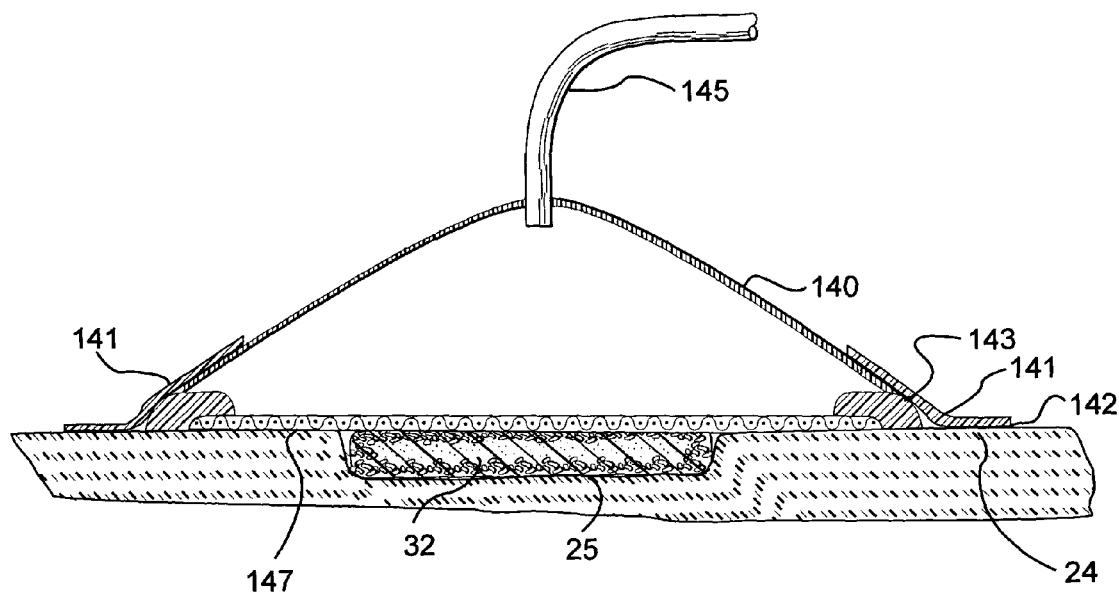
FIG. 3 is a schematic sectional elevational view of a reduced pressure appliance in accordance with another embodiment of the present invention, shown in partial section, in which the reduced pressure appliance includes a rigid, fluid impermeable, cone-shaped wound cover overlying the wound site.

The reduced pressure appliance 30 is not, however, limited to the configuration illustrated in FIG. 1. The appliance 30 may also have a wound cover of almost any size, shape, and configuration adapted to treat the wound. An example of this type of cover 40 is illustrated in the embodiment of the appliance 30 shown in FIG. 3, which has a wound cover 140 comprised of a rigid, fluid impermeable, generally cone-shaped wound cover 140 overlying the wound site 25. Alternatively, the cover overlying the wound site may be comprised of a rigid, fluid impermeable, flat, bowl-shaped, or cup-shaped wound cover to protect the site of a wound 25 from impact or abrasion during treatment. The wound cover may also be comprised of a fluid impermeable, flexible cover supported by rigid support members overlying the wound site 25. All of these cover types may be sealed to the normal skin 24 surrounding the wound 25 by using the suction created under the cover and a soft and flexible padding material 143 around the periphery of the cover 140, which is in contact with the skin 24. More preferably, the cover 140 is sealed to the skin 24 using a fluid-impermeable adhesive material 141 such as an adhesive tape or an adhesive sheet that has been cut to surround and at least partially overlie the periphery of the cover 140. As an additional example, the cover may be comprised of a CPR mask, which may be sealed to the skin surrounding the wound with an inflatable air cuff that is a part of the mask, with a fluid-impermeable adhesive material, or by some other fluid-impermeable means. Where the cover 140 is not in contact with the absorbable matrix 32, and is therefore not exerting force adequate to keep the matrix 32 in place within the wound 25, a rigid or semi-rigid porous screen 147 may be placed over the matrix 32 and under the cover 140 in a position so that the periphery of such screen 147 is held in place by a portion of the cover 140 or the seal 142 that holds the cover 140 in place against the skin 24. In such case, the screen 147 is of a thickness and rigidity necessary to hold the matrix 32 in place within the wound 25, but having a porous structure so that fluids (including gases) are able to pass through the screen 147.

The appliance 30 also includes a suction port in the form of a hollow suction tube 45 that connects with the vacuum system 50 to provide suction within the sealed enclosure. The suction tubing 45 serves as a suction port for the appliance 30. In the embodiment of the invention illustrated in FIG. 1, an end segment 45a of the tubing 45 is embedded within the absorbable matrix 32 for providing suction or reduced pressure within the enclosure provided under the wound cover 40. Embedding the open end of segment 45a of tubing 45 within the interior of the absorbable matrix 32 permits the absorbable matrix 32 to function as a shield to help prevent the wound cover 40 from being inadvertently sucked into sealing engagement with the open end of the tube thereby plugging the tube 45 and restricting gas flow. The tube segment 45a embedded within the absorbable matrix 32 preferably has at least one side port 47 for positioning within the interior of the absorbable matrix 32 to promote substantially uniform application of reduced pressure throughout the enclosure. Positioning the side port 47 of tube segment 45a within the interior of the absorbable matrix 32 permits the absorbable matrix 32 to function as a shield for the side port to thereby prevent the wound cover 40 from being sucked into the side port 47 and thereby restricting gas flow. The open cells of the absorbable matrix 32 facilitate gas flow throughout the enclosure. In addition, the absorbable matrix 32 functions to encourage the growth of tissue in the area of the wound 25 into the matrix 32 and to hold the wound cover 40 generally out of contact with the wound 25 during the application of suction within the enclosure.

Tubing 45 and tube segment 45a are sufficiently flexible to permit movement of the tubing but are sufficiently rigid to resist constriction when reduced pressure is supplied to the appliance 30 or when the location of the wound 25 is such that the patient must sit or lie upon the tubing 45 or upon the reduced pressure appliance 30. The matrix-tube assembly comprising the absorbable matrix 32 and the tube 45 may be fabricated by snaking the end of the tube segment 45a through an internal passageway in the absorbable matrix 32 such as by pulling the end of the tube segment 45a through the passageway using forceps. The matrix-tube assembly 32 and 45 is preferably prepared prior to use under sterile conditions and then stored in an aseptic package.

Figure 4A:
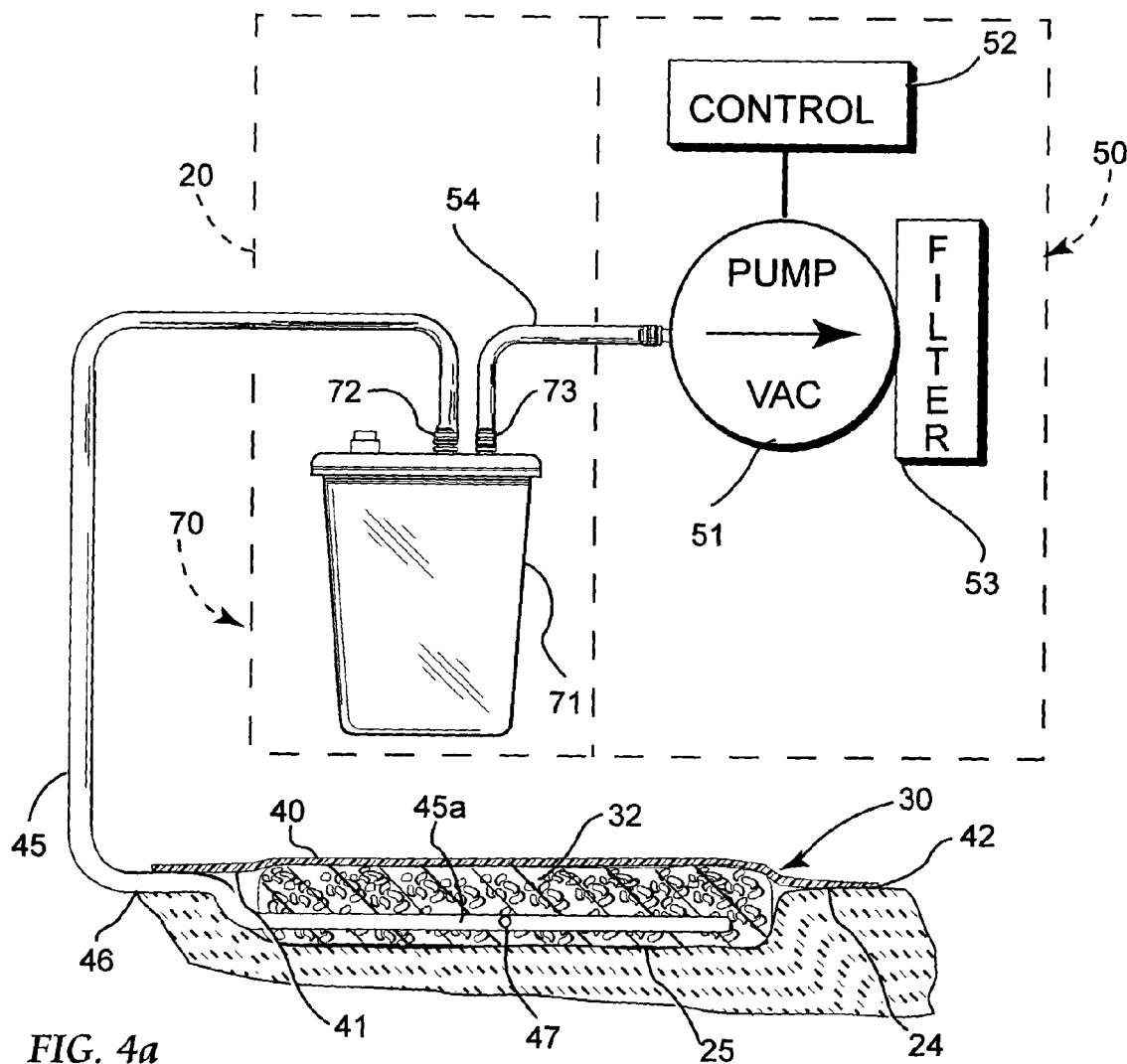
FIG. 4a is a schematic elevational view of a wound treatment apparatus in accordance with a particular embodiment of the present invention in which a reduced pressure appliance, shown in partial section, includes a flexible, fluid impermeable wound cover sealed over the wound and an absorbable matrix positioned in the wound, and in which a vacuum system provides reduced pressure within the wound cover of the appliance.

As shown in FIG. 4a, the vacuum system 50, which produces a source of reduced pressure or suction that is supplied to the reduced pressure appliance 30, includes a vacuum pump 51, a control device 52, a filter 53, and tubing 54 that connects the vacuum pump 51 to the collection system 70. Predetermined amounts of suction or reduced pressure are produced by the vacuum pump 51. The vacuum pump 51 is preferably controlled by a control device 52 such as a switch or a timer that may be set to provide cyclic on/off operation of the vacuum pump 51 according to user-selected intervals. Alternatively, the vacuum pump 51 may be operated continuously without the use of a cyclical timer. A filter 53 such as micropore filter is preferably attached to the exhaust of the pump 51 to prevent potentially pathogenic microbes or aerosols from being vented to atmosphere by the vacuum pump 51.

As shown in FIG. 4a, a fluid collection system, generally designated 70, is interconnected between the suction pump 51 and the appliance 30 to remove and collect any exudate which may be aspirated from the wound 25 by the reduced pressure appliance 30. The appliance 30 functions to actively draw fluid or exudate from the wound 25. Collection of exudate in a fluid collection system 70 intermediate the pump 51 and the appliance 30 is desirable to prevent clogging of the pump 51. The fluid collection system 70 is comprised of a fluid-impermeable collection container 71 and a shutoff mechanism 75. The container 71 may be of any size and shape capable of intercepting and retaining a predetermined amount of exudate. Many examples of such containers are available in the relevant art. The preferred container in this embodiment of the invention is illustrated in side elevation view in FIG. 4a, said container having two openings in the top of the container 71. The container 71 includes a first port 72 at the top opening of the container for sealed connection to suction tubing 45. The first port 72 enables suction to be applied to the reduced pressure appliance 30 through the tubing 45 and also enables exudate from the wound 25 covered by reduced pressure appliance 30 to be drained into the container 71. The container 71 provides a means for containing and temporarily storing the collected exudate. A second port 73 is also provided on the top of the container to enable the application of suction from the vacuum pump 51. The second port 73 of the collection system 70 is connected to the vacuum pump 51 by a vacuum line 54. The collection system 70 is sealed generally gas-tight to enable the suction pump 51 to supply suction to the appliance 30 through the collection system 70.

The container 71 may also include a fluid impenetrable flexible liner within its volume that is used to collect the exudate in a manner that avoids contaminating the container 71 with pathogenic microbes and other harmful matter present in the exudate. In such case, the flexible liner may be directly connected to the first port 72 and second port 73 in a manner so that no exudate comes into direct contact with the container 71. In this embodiment, the preferred liner is a flexible bag constructed of a polymer material, which is connected to the first port 72.

The vacuum system 50 and collection system 70 preferably include a shutoff mechanism for halting or inhibiting the supply of the reduced pressure to the appliance 30 in the event that the exudate aspirated from the wound 25 exceeds a predetermined quantity. Interrupting the application of suction to the appliance 30 is desirable to prevent exsanguination in the unlikely event a blood vessel ruptures under the wound cover 40 during treatment. If, for example, a blood vessel ruptures in the vicinity of the wound 25, a shut-off mechanism would be useful to prevent the vacuum system 50 from aspirating any significant quantity of blood from the patient.

Figure 4B:
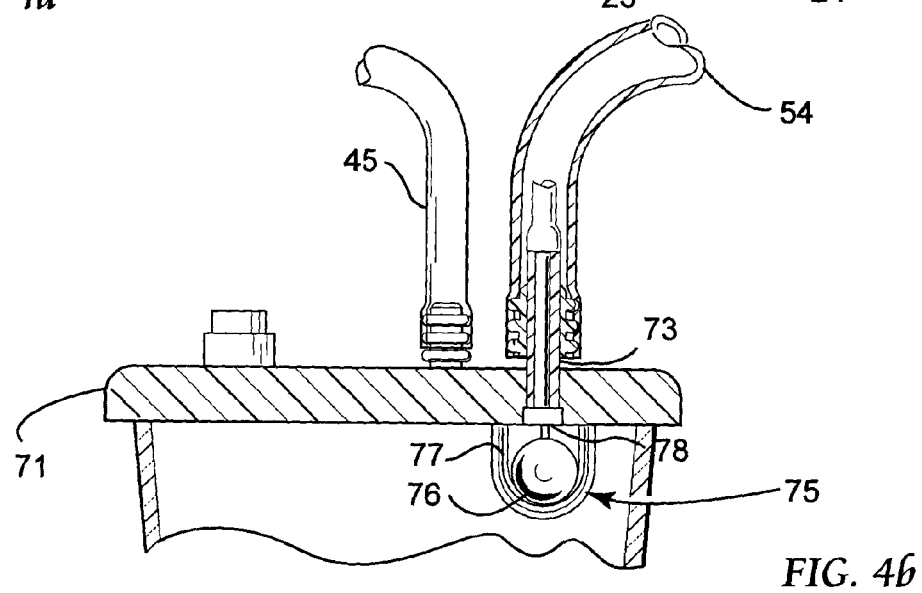

The shutoff mechanism 75 may be comprised of any means that enables the vacuum system 50 to halt the supply of reduced pressure to the wound cover 40 at any time that the volume of exudate from the wound 25 exceeds a predetermined amount. Such means may include mechanical switches, electrical switches operably connected to the vacuum system controller 52, optical, thermal or weight sensors operably connected to the vacuum system controller 52, and any other means that are currently known in the relevant art or which may hereafter be discovered. The shutoff mechanism 75, as illustrated in FIG. 4b, is preferably a float valve assembly in the form of a ball 76 which is held and suspended within a cage 77 positioned below a valve seat 78 disposed within the opening at the top of the container below the second port that will float upon the exudate and will be lifted against the valve seat 78 as the container fills with exudate. When the ball 76 is firmly seated against the valve seat 78, the float valve blocks the second port 73 and thereby shuts off the source of suction from the vacuum system 50. Other types of mechanisms may also be employed to detect the liquid level within the container 71 in order to arrest operation of the vacuum system 50.

Figure 5E:
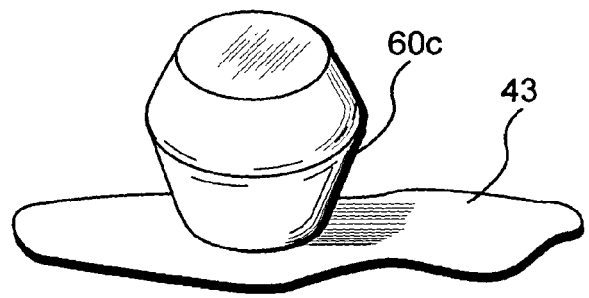
FIG. 5e is a schematic sectional elevational view of the reduced pressure appliance of FIG. 5a, illustrating alternative protrusions having a bellows-type of configuration.
Figure 5F:
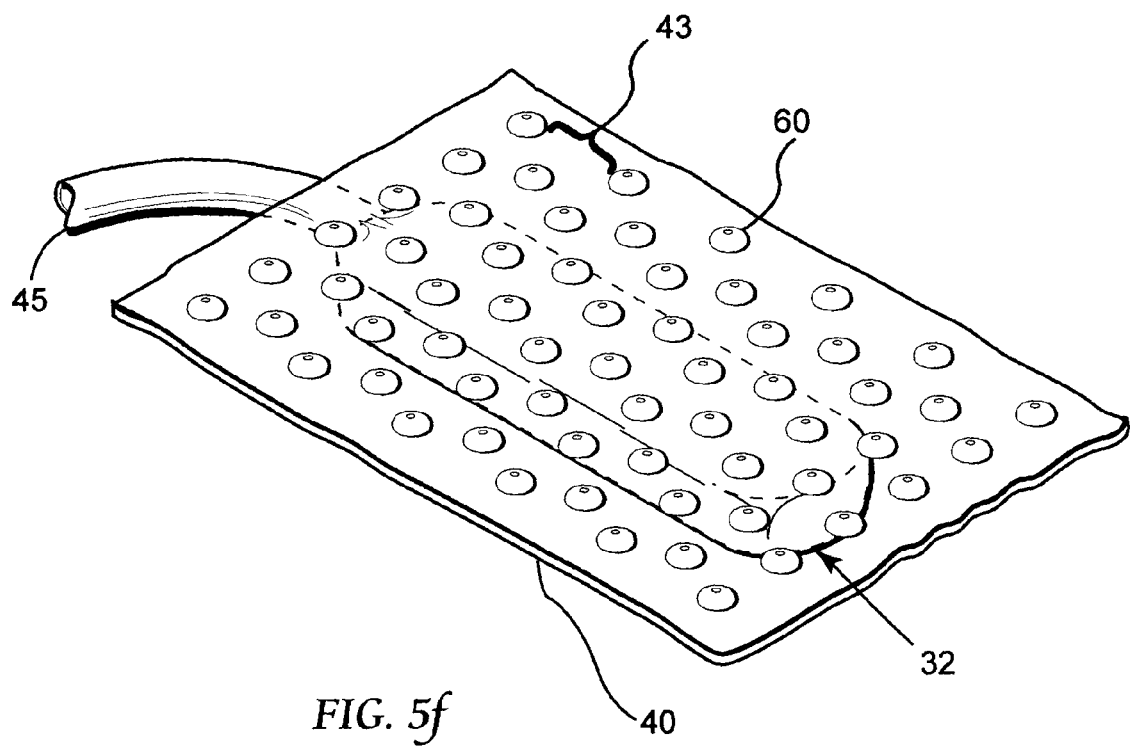
FIG. 5f is a perspective view of the reduced pressure appliance of FIG. 5a, illustrating a pattern of protrusions on the wound cover.

In another version of the invention, the wound treatment apparatus includes means to monitor the pressure beneath the wound cover 40 at the site of the wound 25. In one embodiment of this version of the invention, as illustrated in FIG. 5a, the wound cover 40 has a plurality of protrusions 60 in the form of hills or bumps embedded in the cover 40. As illustrated in FIG. 5a, the protrusions 60 protrude above the remaining surface 43 of the cover 40 when the cover 40 is not in use for wound treatment. A detailed view of a protrusion 60a in this configuration is shown in perspective view in FIG. 5b. Generally, as illustrated in FIG. 5c, in some embodiments, when the cover 40 is in use (i.e., sealed over the wound site 25 with reduced pressure applied beneath the cover 40), the protrusions 60 are displaced inwardly (or downward when the cover 40 is in the orientation depicted in FIG. 5c) so that they are depressed to a level almost the same as that of the remaining surface 43 of the cover 40. A detailed view of a protrusion 60b in the depressed configuration is shown in perspective view in FIG. 5d. In another embodiment, the protrusions 60c are configured in the form of bellows, as shown in FIG. 5e. In this version of the invention, as the pressure beneath the cover 40 decreases (i.e., the level of reduced pressure increases), the top of the protrusion 60c is displaced downward toward the level of the remaining surface 43 of the cover 40. The protrusions 60 may be placed in any location, as well as in any pattern or lack of pattern, on the surface of the cover 40. An example of one possible pattern is illustrated in FIG. 5f.

The protrusions 60 may be constructed of the same material as the remainder of the cover 40, or may be constructed of a material different from the remainder of the cover 40, depending upon the sensitivity of pressure monitoring desired. Similarly, the protrusions 60 may be constructed of material having the same thickness as the remainder of the cover 40, or material of a different thickness, depending upon the sensitivity of pressure monitoring desired. For example, if the reduced pressure beneath the cover 40 is of a relatively low level, so that the difference between the ambient atmospheric pressure above the cover 40 is relatively small when compared to the reduced pressure beneath the cover 40, it may be desirable to have the protrusions 60 be able to change shape with relatively small changes in pressure beneath the cover 40 during the treatment period. In such case, it may be preferable to have the protrusions 60 of a thickness less than the thickness of the remaining cover material. It may also be preferable to have the protrusions 60 constructed of a material more pliable than the material of which the remainder of the cover 40 is constructed. Similarly, if the reduced pressure beneath the cover 40 is of a relatively high level, so that the difference between the ambient atmospheric pressure above the cover 40 is relatively large when compared to the reduced pressure beneath the cover 40, it may be desirable to have the protrusions 60 be able to change shape with relatively large changes in pressure beneath the cover 40 during the treatment period. In such case, it may be preferable to have the protrusions 60 of a thickness more similar to the thickness of the remaining cover material. It may also be preferable to have the protrusions 60 constructed of a material that is more similar to the material of which the remainder of the cover 40 is constructed in terms of pliability.

By preselecting the thickness and pliability of the material used to construct the protrusions 60, it may also be possible to monitor the pressure by partial deflections of the protrusions 60. For example, the protrusions 60 may be displaced in an increasing amount above the remaining surface 43 of the cover 40 as the pressure beneath the cover 40 increases (i.e., the level of reduced pressure decreases). This relationship of displacement of the protrusions 60 to the increase in pressure beneath the cover 40 may be linear or based upon some other function. Similarly, the protrusions 60 may be constructed so that they only begin to be displaced when a predetermined pressure differential occurs between the area under the cover 40 and the area above the cover 40. It should be noted, however, that this version of the invention is intended as a means to provide an inexpensive and approximate visual indication of the occurrence of loss of reduced pressure beneath the cover and may not be a means to accurately measure the actual pressure beneath the cover or the actual difference between the pressure above the cover and the reduced pressure beneath the cover.

As a result, the preferable thicknesses and materials to be used in constructing the cover 40 and protrusions 60 in this version of the invention are dependent upon a multitude of factors, including the desired pressure beneath the cover 40. Preferably, the wound cover 40 is constructed of polyurethane, having a thickness of only a few mils to ⅛th inch, and having protrusions 60 constructed of the same material as the remaining portion of the cover 40, said protrusions 60 having a thickness only slightly less than the thickness of the cover 40 to a relatively small fraction of the thickness of the cover 40.

Further, the protrusions 60 may be constructed of material that is of a different color than the color of the remaining surface 43 of the cover 40. Similarly, the protrusions 60 may be of a different shade of the same color as the remaining surface 43 of the cover 40. As the protrusions 60 are displaced away from the remaining surface 43 of the cover 40, the protrusions 60 may change color as a result of the expansion of the material comprising the protrusions 60.

In another embodiment of this version of the invention, the protrusions work in the manner opposite to that described above. In this embodiment, the cover has within it a plurality of areas that are displaced away (i.e., pulled down) from the remaining surface of the cover toward the wound when reduced pressure is applied beneath the cover. This downward displacement is the result of the reduced pressure suction, which causes tension that pulls the protrusions away from the remaining surface of the cover. As the pressure beneath the cover increases, the tension on the protrusions weakens allowing the protrusions to recede back into the cover. The principles discussed above with respect to thickness, materials, color, and partial deflection monitoring of pressure apply to this embodiment of the invention as well. It should be noted that bellows-type protrusions are not used in this embodiment.

The protrusions 60 may also have a means whereby they produce an audible sound as the protrusions 60 are being displaced away from the remaining surface 43 of the cover 40. This sound may be produced by the "crinkling" or vibration of the material as it is displaced away from the remaining surface 43 of the cover 40.

It should be noted that the means to monitor the pressure beneath the cover described in this embodiment of the invention may be used independently of any other feature of this invention. In addition, the means to monitor pressure beneath the cover is not limited to use in treatment of open wounds, decubitus ulcers, dehisced incisions, partial thickness burns, and various lesions to which flaps or grafts have been attached. Instead, said pressure monitoring means may be used in any application involving reduced pressure in the treatment of any portion of the body of a patient, such as cosmetic surgery, cosmetic healing, and prophylactic suctioning for cosmetic and psychological reasons. In addition, the cover may be of any configuration, including the cover configurations specifically discussed above. Further, it is not necessary that any packing material or matrix be present in the area of the wound beneath the cover in this version of the invention. Nor is it necessary that the features included in this version of the invention be included as a part of any other version or embodiment of this invention.

Figure 6:
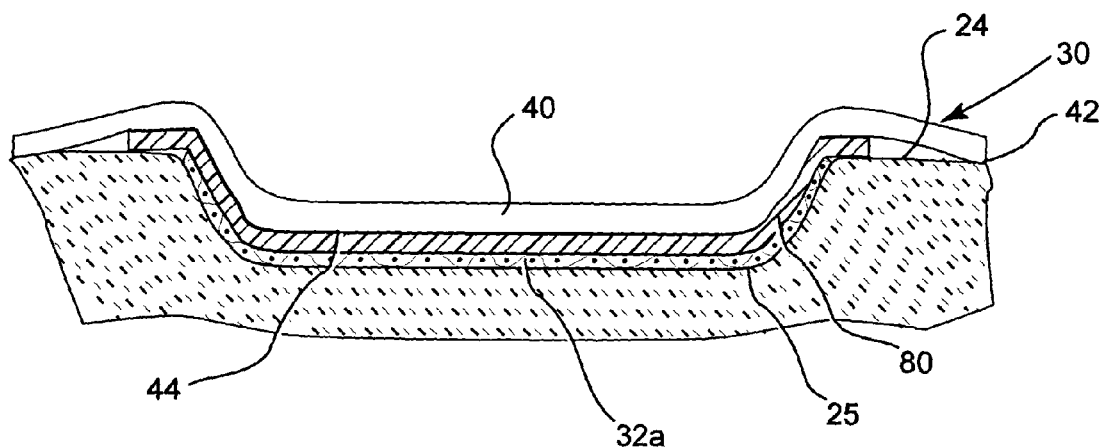
FIG. 6 is a schematic sectional elevational view of a reduced pressure appliance in accordance with another embodiment of the present invention, shown in partial section, in which the reduced pressure appliance includes a packing material or an absorbable matrix positioned in the wound, and a flexible, fluid impermeable wound cover sealed over the wound, and a layer of temperature sensitive material located between the cover and the wound.

In another version of the invention, the wound treatment apparatus includes means to monitor the temperature in the area of the wound 25. In one embodiment of this second version of the invention, as illustrated in FIG. 6, a layer of temperature sensitive material 80 is placed adjacent to the lower surface 44 of the wound cover 40. Alternatively, the cover 40 and the layer 80 may be joined together to form a single integrated unit. In such case, the cover 40 and the layer 80 may be joined in any manner that is fluid-impermeable and allows the color (or other property exhibiting the change of temperature) of the temperature sensitive layer 80 to be observed from above the wound cover 40. The preferred means to join the cover 40 and the layer 80 is a transparent or semi-transparent adhesive material. Alternatively, the wound cover 40 may itself be composed of a temperature sensitive material, so that a separate temperature sensitive layer is not required.

The temperature sensitive layer 80 (or the cover 40, if it is composed of a temperature sensitive material) may be composed of any material that changes properties in a manner that does not adversely affect the operation of the reduced pressure appliance 30. Preferably, the temperature sensitive layer 80 is composed of a material that changes color, or changes from one shade of a color to another shade of the same color, as the temperature of the material changes. The change in color or shade preferably occurs within the temperature range that may be expected in the area of the wound 25. In other words, the change in color or shade of the material should be significant enough to adequately indicate changes in temperature within the range of temperatures expected in the area of the wound 25. More preferably, the temperature sensitive material is a material that changes color in the range from approximately 95 degrees Fahrenheit to approximately 105 degrees Fahrenheit.

In the embodiment of the invention shown in FIG. 6, the temperature sensitive layer 80 is placed over a packing material or matrix 32a, which packing material or matrix 32a is placed within the area of the wound 25. The matrix 32a may be an absorbable matrix 32a, as described above. The packing material may be constructed of any material that is suitable for placement within a wound 25, which may be to prevent its overgrowth, but still allows for fluid and gas flow to and from the wound 25, such as a porous polymer material or gauze. In order to provide for uniform temperature monitoring, the packing material or matrix 32a is preferably of relatively uniform thickness when placed within the area of the wound 25. In addition, the packing material or matrix 32a should be thin enough to allow for the temperature of the tissue to affect the temperature of the temperature sensitive layer 80. More preferably, the thickness of the packing material or matrix 32a should not exceed slightly greater than zero to one half inches. The packing material or matrix 32a may, however, be of non-uniform thickness where the temperature sensitive layer 80 is comprised of temperature sensitive material in a manner that compensates for the differences in thickness of the packing material or matrix 32*a*.

The wound cover 40 is placed over the temperature sensitive layer 80 and sealed to the normal skin 24 surrounding the wound 25. If the cover 40 and the temperature sensitive layer 80 are an integrated unit, however, the unit is placed over the packing material or matrix 32*a* without a separate temperature sensitive layer 80. If the cover 40 is composed of a temperature sensitive material, it is placed over the packing material or matrix without an additional temperature sensitive layer 80. It should be noted, however, that the temperature sensitive material used in this embodiment of the invention is intended as a means to provide an approximate visual indication of the temperature in the area of the wound 25 beneath the cover 4, and may not accurately measure the actual temperature beneath the cover 40.

Figure 7:
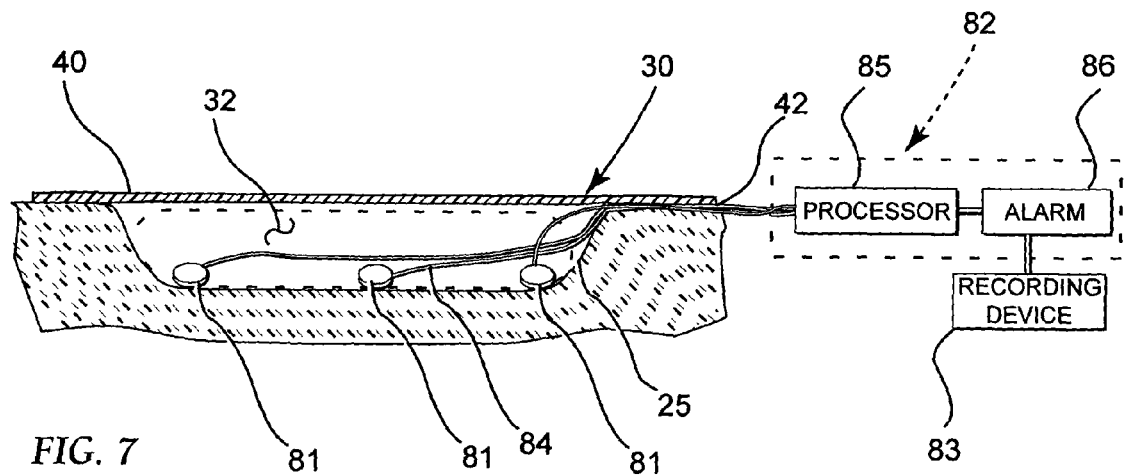
FIG. 7 is a schematic sectional elevational view of a reduced pressure appliance in accordance with another embodiment of the present invention, shown in partial section, in which the reduced pressure appliance includes a packing material positioned in the wound, and a flexible, fluid impermeable wound cover sealed over the wound, and a plurality of temperature sensors located at and surrounding the site of the wound, and in which an alarm system and a temperature display and recording device are connected to the temperature sensors.

In another embodiment of this second version of the invention, one or more temperature measuring devices 81 are placed within the area of the wound 25 and connected to an alarm system, generally designated as 82. The temperature measuring devices 81 may also be connected to a temperature display and recording device 83. An example of this embodiment is illustrated in FIG. 7, which shows temperature measuring devices 81 placed in the area of the wound 25. The temperature measuring devices 81 may be placed in any area of the wound 25 and the reduced pressure appliance 30. For example, the temperature measuring devices 81 may be placed adjacent to and in direct contact with the tissue in the area of the wound 25. Alternatively, the temperature measuring devices 81 may be embedded in any packing material or matrix 32 placed in the area of the wound 25, or in the area between such packing material or matrix 32 and the cover 40, or embedded within the cover 40, or adjacent to either surface of the cover 40.

The temperature measuring devices 81 are preferably capable of measuring temperatures in the range of temperatures expected in the area of the wound 25. More preferably, the temperature measuring devices 81 are capable of measuring temperatures in the range of 95 degrees Fahrenheit to 105 degrees Fahrenheit. The temperature measuring devices 81 may be any device that measures temperature in the desired range and produces a corresponding signal that may be interpreted by the alarm system 82 and temperature display and recording device 83. The temperature measuring devices 81 must, however, not be harmful to body tissue. The temperature measuring devices 81 are preferably thermocouples or optical sensors or detectors. The temperature measuring devices 81 are more preferably thermocouples that generate an electronic signal representing the temperature measured by the thermocouple.

The temperature measuring devices 81 are connected by leads 84 to an alarm system 82. The leads 84 may be in any form compatible with the temperature measuring devices 81 and the alarm system 82 and recording device 83. Preferably, the leads 84 are cables or wires constructed of an electrically conductive material, optical fiber, or other medium enabling data transmission that transfers the signals from the temperature measuring devices 81 to the alarm system 82 and the display and recording device 83. Leads 84 placed under the wound cover 40 feedthrough the seal 42 beneath the cover 40 in a manner similar to that for the tubing (as illustrated and discussed above in connection with FIG. 1) that maintains the fluid impermeable nature of the seal 42.

The alarm system 82 is comprised of a computer or other data processor 85 and an alarm device 86. The computer or data processor 85 receives the signals from the temperature measuring devices 81 and converts them to electronic or other signals that are recognized by the alarm device 86. The computer or data processor 85 is of a type that is commonly available in the relevant art. The alarm device 86 may produce any type of audible sound as an alarm, such as a ringing sound, buzzing, chirping or other common alarm noise. Alternatively, the alarm device 86 may include a digitally produced audible voice that presents predetermined messages corresponding to different temperature conditions in the area of the wound 25. The alarm device 86 preferably produces different levels of alarm depending upon the temperature measurements received from the temperature measuring devices 81. For example, as the temperature drops below or rises above successive preselected values of temperature, as measured by any temperature measuring device 81, the alarm device 86 may sound successive predetermined alarm pitches, sounds, messages or series of sounds. Similarly, as the temperature measured by multiple temperature measuring devices 81 successively falls below or rises above a preselected temperature, the alarm device 86 may sound successive predetermined alarm pitches, sounds, messages or series of sounds. The alarm system 82 may also be connected to the vacuum supply 50, so that upon production of a predetermined alarm by the alarm device 86, the vacuum pump controller 52 causes the pump 51 to cease operation.

The computer or data processor 85 may also be connected to a temperature display and recording device 83 that records the temperatures measured by one or more of the temperature measuring devices 81. The temperature recording device 83 may be any device designed to record or display data that is compatible with the signals produced by the computer or data processor 85. Such devices are preferably devices that record data on compact disks, floppy disks, magnetic tape, integrated circuits, or other similar media in digital form or "manual" devices that record or display data in a visually depicted form, such as a chart recorder or visual electronic display, such as an LCD or CRT monitor. The more preferred temperature display and recording device 83 is a device recording data on a compact disk used in conjunction with an LCD monitor.

It should be noted that in this embodiment of this version of the invention the cover 40 may be of any configuration, including the cover configuration illustrated in FIG. 3 and the other cover configurations specifically discussed above in connection with FIG. 3. In addition, it is not necessary that any packing material or matrix 32 be present in the area of the wound 25 beneath the cover 40 in this version of the invention. It is also not necessary that the temperature display and recording device 83 be included in every embodiment of this version of the invention. Nor is it necessary that the features included in this version of the invention be included as a part of any other version or embodiment of this invention.

Figure 8A:
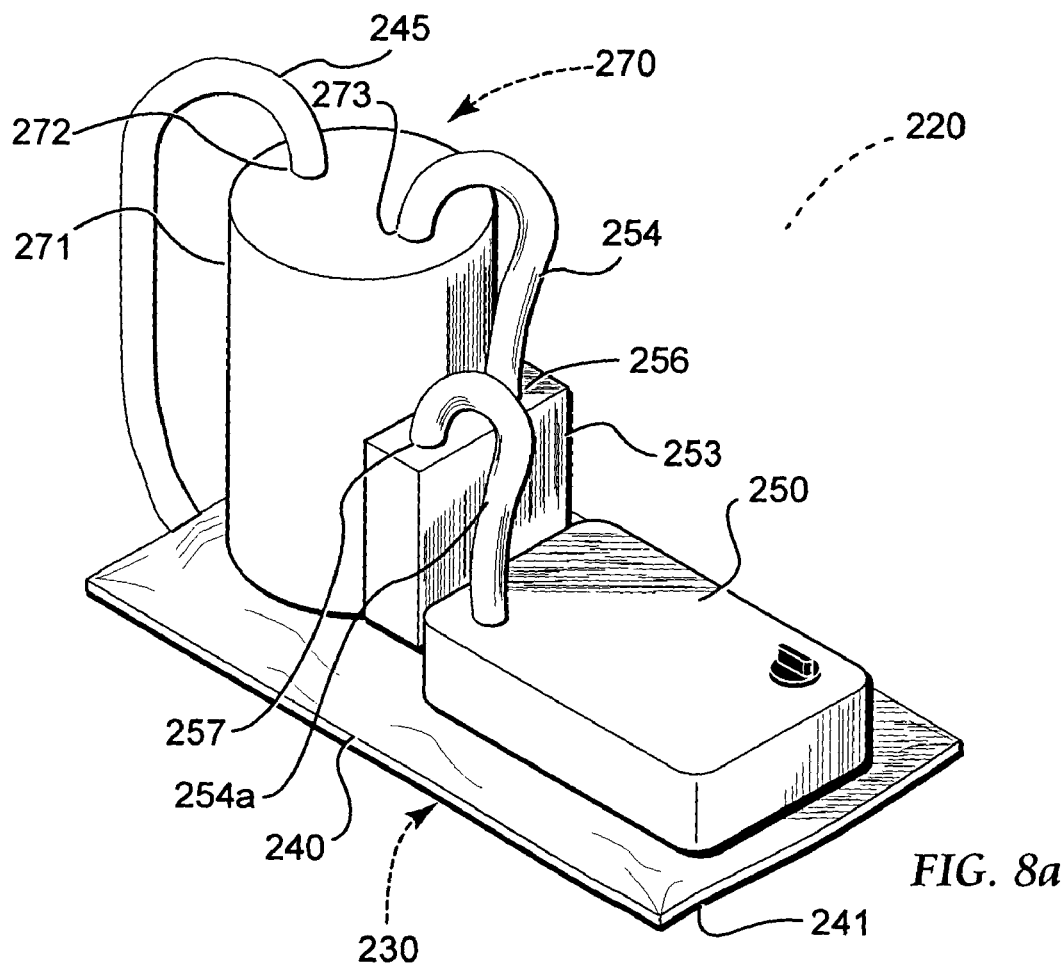
FIG. 8a is a perspective view of a wound treatment apparatus in accordance with another embodiment of the present invention, shown from above, in which a reduced pressure appliance, a vacuum source, a filter, and a fluid collection system are connected together as a compact and portable apparatus.

In another version of the invention, the wound treatment apparatus 220 is portable and may be self-contained. In a first embodiment of this version of the invention, as illustrated in FIG. 8*a*, a miniature and portable vacuum source 250 is connected to a wound cover. The vacuum source 250 is preferably a miniature and portable vacuum pump. The vacuum source 250 may also be connected to a filter 253, which is connected to a collection system 270. The vacuum source 250 is used to provide suction to the reduced pressure appliance, generally designated as 230. It is portable in the sense that it is of a size small enough to be positioned directly on the surface of the wound cover 240. The vacuum source 250 is also lightweight to avoid placing too much pressure on any body part being treated by the apparatus 220 and to allow the apparatus 220 to be easily transported. The vacuum source 250 may be powered by electricity received through a cord plugged into a standard wall socket, or the vacuum source 250 may be powered by a battery, fuel cell, or other alternative means, such as solar or photo electric sells or a windmill or watermill operated generator. The vacuum source 250 may also be operated by other means, such as pneumatics or hydraulics, if such means are available.

The wound cover 240 may be of almost any size, shape, and configuration adapted to treat the wound. Thus, the wound cover 240 is not limited to the embodiment illustrated in FIG. 8a. As illustrated and discussed above in relation to FIG. 3, the cover may be comprised of a rigid, fluid impermeable, cone-shaped, bowl-shaped, or cup-shaped wound cover to protect the site of a wound 25 from impact or abrasion during treatment. Alternatively, the cover may be comprised of a flexible or rigid flat wound cover.

The vacuum source 250 may be attached to the cover 240 using any means that is compatible with the structure of the cover 240 and the vacuum source 250. For example, if the cover 240 is constructed of a flexible, fluid impermeable material, the vacuum source 250 may be attached to the cover 240 using an adhesive material, such as a glue or other liquid or sprayed adhesive, adhesive tape, and similar means that are currently known in the relevant art or which may hereafter be discovered. As another example, if the wound cover 240 is constructed of a rigid material, the vacuum source 250 may be attached to the cover 240 using a variety of fasteners and similar means, such as anchors, bolts, rivets, screws, nuts, latch and clasp, hook and loop fasteners (such as that commonly sold under the trade name VELCRO), ultrasonic welding, and similar structures that are currently known in the relevant art or which may hereafter be discovered. The vacuum source 250 may therefore be permanently attached to the cover 240, or the vacuum source 250 may be removably attached to the cover 240 allowing the vacuum source 250 to be reused after being used for a treatment even if the cover 240 is no longer usable after such treatment. The means of fastening the vacuum source 250 to the cover 240 must, however, be accomplished in a manner that allows the cover 240 to maintain the desired reduced pressure beneath the cover 240 while it is in use. Thus, gasket or sealant material may be used to seal any areas of perforation of the cover 240 where the fastener penetrates the surface of the cover 240.

Figure 8B:
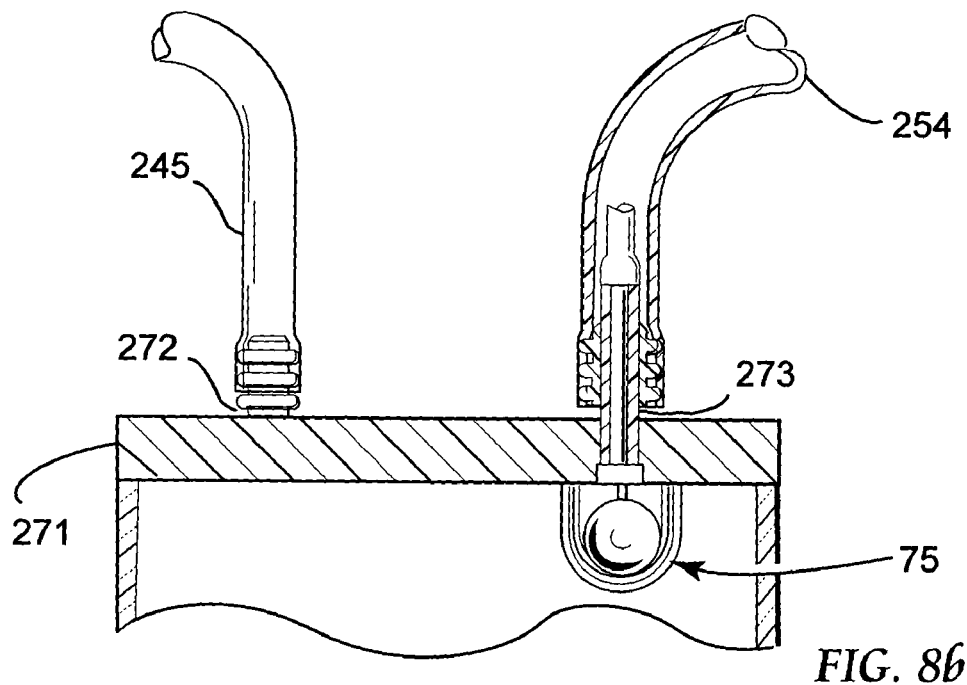

The fluid collection system 270 in the embodiment illustrated in FIG. 8a includes a container 271 to collect the exudate and a shutoff mechanism 275, one embodiment of which is illustrated in FIG. 8b, to halt operation of the vacuum source 250 if the level of exudate in the container 271 exceeds a predetermined level. The container 271 is of the minimum size desired to collect and maintain the amount of exudate expected to be aspirated from the wound during the time of anticipated use of the portable wound treatment apparatus 220. Alternatively, a small container 271 may be used, in which the fluid is changed intermittently as necessary during the treatment period. The container 271 has two ports, a first port 272 for connecting the container 271 to the reduced pressure appliance 230 and a second port 273 for connecting the container 271 to the vacuum source 250. A filter 253 may also be connected intermediate the vacuum source 250 and the container 271. The shutoff mechanism may be comprised of any means that enables the vacuum system 250 to halt the supply of reduced pressure to the wound cover 240 at any time the volume of exudate from the wound exceeds a predetermined amount to prevent, thereby preventing such exudate from contaminating the vacuum source 250. Such means may include mechanical switches, electrical switches operably connected to the vacuum source 250, optical, thermal or weight sensors operably connected to the vacuum source 250, and any other means that are currently known in the relevant art or which may hereafter be discovered. Where the shutoff mechanism transfers electrical or other data signals to the vacuum source 250, the vacuum source 250 may contain a control mechanism to convert said signals to the form necessary to halt the production of reduced pressure by the vacuum source 250. Such means is preferably the float valve shutoff mechanism 275 illustrated in FIG. 8b, connected to the second port 273 of the container 271, which has the same features as the float valve illustrated in and discussed above in connection with FIG. 4a.

As illustrated in FIG. 8a, this embodiment of the invention may also include a filter 253 to prevent potentially pathogenic microbes or aerosols from contaminating the vacuum source 250. The filter 253 is generally comprised of a filter element encased in a fluid impermeable housing that has an inlet port 256 and an outlet port 257. The filter element is preferably a hydrophobic and micropore filter capable of filtering out pathogenic microbes or aerosols. The housing of the filter 253 may be constructed in a manner that enables the filter element to be changed if desired. The filter 253 need not, however, be used in every embodiment of this version of the invention.

In the embodiment illustrated in FIG. 8a, tubing 245 is used to connect the reduced pressure appliance 230 covering a wound 225 to the collection system 270 by means of the first port 272 located on the container 271. The features of this tubing 245 and reduced pressure appliance 230 are substantially the same as illustrated and discussed above in connection with FIG. 1 and FIG. 4a. In addition, in the embodiment of the invention illustrated in FIG. 8a, the second port 273 of the container 271 is connected to the inlet port 256 of the filter 253 by flexible vacuum tubing 254, such as that used to connect the collection system 270 to the reduced pressure appliance 230. This is not, however, the only means of connecting the collection system 270 to the filter 253. For example, the connection may be made by using a rigid, fluid impermeable structure, such as a short length of rigid polymer tube, permanently connecting the filter 253 and the collection system 270. The filter 253 may also be directly attached to the container 271 without the use of any tubing or other means, causing the container 271 and the filter 253 to be integrated as a single unit. In the embodiment of the invention illustrated in FIG. 8a, the outlet port 257 of the filter 253 is connected to the vacuum source 250 by flexible vacuum tubing 254a, such as that used to connect the collection system 270 to the reduced pressure appliance 230. This is not, however, the only means of connecting the collection system 270 to the filter 253. For example, the connection may be made by using a rigid, fluid impermeable structure, such as a short length of rigid polymer tube permanently connecting the filter 253 and the vacuum source 250. The filter 253 may also be directly attached to the vacuum source 250 without the use of any tubing or other means, causing the container 271 and the filter 253 to be integrated as a single unit. As illustrated in FIG. 8a, the vacuum source 250, the filter 253, and the container 271 may also be directly attached to one another to form a single integrated unit. Such attachment may be made by any of the means described above that may be used to attach the vacuum source 250 to the cover 240.

Use of the wound treatment apparatus can be illustrated by a prospective example involving a reduced pressure appliance 30 of the type discussed in connection with FIG. 1. After preparing the bed of the wound 25, one end of a length of vacuum tubing 45 is embedded in an absorbable matrix 32 that is trimmed to be the size and shape of the wound 25. The matrix 32 is saturated with saline and placed in the wound 25.

As illustrated in FIG. 7, if temperature monitoring is desired, temperature measuring devices 81 are placed in the desired locations and connected to an alarm system 82, and if desired, a display and recording device 83. Alternatively, a temperature sensitive layer 80 is placed over the matrix, as illustrated in FIG. 6. A fluid impermeable or gas impermeable flexible adhesive sheet 40, such as IOBAN, is placed over the matrix 32 (and temperature measuring means, if utilized) and the wound 25 and sealed to the normal skin 24 surrounding the wound 25. The site of feedthrough of the vacuum tube 45 and any leads 84 from under the cover 40 is then sealed with a liquid or paste adhesive. Negative pressure is then applied to the reduced pressure appliance 30 by the vacuum system 50, through the intermediate fluid collection system 70.

Negative pressure appliances are useful for treating a variety of wounds. Treatment of a wound can be carried out by securing a negative pressure appliance to the treatment site as previously shown and described, and then maintaining a substantially continuous or cyclical reduced pressure within the appliance until the wound has reached a desired improved condition. A selected state of improved condition may include formation of granulation tissue sufficient for the attachment of a flap or graft, reduction of microbial infection in the wound, arrest or reversal of burn penetration, closure of the wound, integration of a flap or graft with the underlying wounded tissue, complete healing of the wound, or other stages of improvement or healing appropriate to a given type of wound or wound complex.

It may be preferable to change the appliance periodically during treatment, particularly when using appliances incorporating a packing material on or in the wound. The time between changing the appliance where an absorbable matrix is placed on or in the wound would ordinarily be a greater time interval that is generally dependent upon the nature of the wound. Where it is necessary to change the absorbable matrix during the treatment period, it may also be necessary to remove a portion of the matrix, but leave in place the portion of the matrix into which there has been significant tissue growth. In such cases, the portion of the matrix without significant tissue growth incorporated therein should be carefully removed by cutting or tearing away such portion from the remaining portion. New absorbable material can be placed in the area from which the prior material has been removed.

The wound treatment apparatus is preferably operated using a negative or reduced pressure ranging from 0.01 to 0.99 atmospheres, and more preferably practiced using a negative or reduced pressure ranging between 0.5 to 0.8 atmospheres. The time period for use of the wound treatment apparatus on a wound may preferably be at least 12 hours, but can be, for example, extended for one or more days. There is no upper limit beyond which use of the wound treatment apparatus is no longer beneficial; use of the wound treatment apparatus increases the rate of closure up to the time the wound actually closes. Satisfactory treatment of various types of wounds has been obtained via the use of reduced pressures equivalent to about 2 to 7 in. Hg below atmospheric pressure.

Supplying reduced pressure to the appliance in an intermittent or cyclic manner has also been demonstrated to be useful for treating wounds. Intermittent or cyclic supply of reduced pressure to an appliance may be achieved by manual or automatic control of the vacuum system 50. A cycle ratio, the ratio of "on" time to "off" time, in such an intermittent reduced pressure treatment may be as low as 1:10 or as high as 10:1. The preferred ratio is approximately 1:1 which is usually accomplished in alternating 5 minute intervals of reduced pressure supply and non-supply.

A suitable vacuum system 50 includes any suction pump capable of providing at least 0.1 pounds of suction to the wound, and preferably up to three pounds suction, and most preferably up to fourteen (14) pounds suction. The pump can be any ordinary suction pump suitable for medical purposes that is capable of providing the necessary suction. The dimension of the tubing interconnecting the pump and the reduced pressure appliance is controlled by the pump's ability to provide the suction level needed for operation. A ¼ inch diameter tube may be suitable.

In treating damaged tissue, use of the invention usually comprises the steps of applying negative pressure to a wound for a selected time and at a selected magnitude sufficient to reduce bacterial density in the wound. Open wounds are almost always contaminated with harmful bacteria. The application of negative pressure to a wound appears to reduce the bacterial density of the wound. It is believed that this effect is due to either the bacteria's incompatibility with a negative pressure environment or the increased blood flow to the wound area, as blood brings with it cells and enzymes to destroy the bacteria.

Burns may generally be treated using a method that comprises the steps of applying negative pressure to the burn over an area with predetermined reduced pressure and for a time sufficient to inhibit formation of a full thickness burn. A partial thickness burn, one which has a surface layer of dead tissue and an underlying zone of stasis, is often sufficiently infected so that it will transform within 24-48 hours into a full thickness burn, one in which all epidermal structures are destroyed. The application of negative pressure to the wound prevents the infection from becoming sufficiently severe to cause destruction of the underlying epidermal structures. The magnitude, pattern, and duration of pressure application can vary with the individual wound.

What is claimed is:

1. An appliance for administering a reduced pressure treatment to a wound, comprising:
   a cover adapted to cover the wound and adapted to maintain reduced pressure between the cover and the wound; and
   an absorbable matrix adapted to encourage growth of the tissue in the area of the wound into the matrix, said absorbable matrix being located between the wound and the cover;
   wherein:
   the absorbable matrix comprises a first absorbable portion formed from a first material having a first rate of absorption of tissue into the first absorbable portion and a second absorbable portion formed from a second material having a second rate of absorption of tissue into the second absorbable portion, the first material being different than the second material and the first rate of absorption being different than the second rate of absorption;
   the cover comprises a temperature-sensitive material configured such that a user or practitioner can monitor the temperature at the site of the wound by monitoring the appearance of the cover.

2. The appliance of claim 1, wherein the first rate of absorption is greater than the second rate of absorption, and the absorbable matrix is positioned in the wound such that the first absorbable portion is generally adjacent to the deepest portion of the wound and the second absorbable portion is generally closer to the cover than the first absorbable portion.

3. The appliance of claim 1, wherein the appliance further comprises an adhesive material on at least a portion of the cover, the adhesive material being adapted to at least secure a portion of the cover to the tissue surrounding the wound.

4. The appliance of claim 1, further comprising:
a vacuum system adapted to produce a reduced pressure;
a collection system that is operably connected to the vacuum system, and
reduced pressure supply means for connection with the vacuum system adapted to supply the reduced pressure within the cover to the wound.

5. The appliance of claim 4, wherein the reduced pressure provided by the vacuum system is from about 2 in. Hg below atmospheric pressure to about 7 in. Hg below atmospheric pressure.

6. The appliance of claim 4, wherein the reduced pressure supply means comprises a length of tubing, and further comprising a flotation valve within the container for blocking the tubing when a predetermined amount of fluid is collected within the container.

7. The appliance of claim 1, further comprising a conduit configured to communicate with a source of reduced pressure and a space between the cover and the wound so as to transfer the reduced pressure supplied by the source of reduced pressure to the space between the cover and the wound.

8. The appliance of claim 1, further comprising a third absorbable portion formed from a third material having a third rate of absorption of tissue into the third absorbable portion, the third rate of absorption being different than the first rate of absorption and the second rate of absorption.

9. The appliance of claim 1, wherein the first absorbable portion substantially surrounds the second absorbable portion.

10. The appliance of claim 1, wherein the cover comprises a material that is configured to change appearance when the temperature at the site of the wound changes, wherein such material is supported by the cover.

11. The appliance of claim 1, wherein the cover is a flexible sheet.

12. An appliance for monitoring pressure during treatment of any body part of a patient, comprising a cover adapted to cover the body part being treated and adapted to maintain reduced pressure at the site of the body part being treated, wherein:
the cover comprises a plurality of protrusions, each of which is spaced apart from the other protrusions across an outside surface of the cover and configured to indicate whether a predetermined level of reduced pressure is achieved in the space between the cover and the site of the body part being treated beneath the cover; and
each protrusion comprises at least one surface that is configured to be exposed to the space between the cover and the site of the body part being treated beneath the cover.

13. The appliance of claim 12, wherein the appliance further comprises an adhesive material on at least a portion of the cover, the adhesive material being adapted to at least secure a portion the cover to the tissue surrounding the wound.

14. The appliance of claim 12, wherein the plurality of protrusions are configured to displace inwardly as the reduced pressure between the cover and the wound increases such that the amount of inward displacement of the protrusions increases as the reduced pressure between the cover and the wound increases.

15. The appliance of claim 12, wherein the plurality of protrusions supported by the cover are configured to displace inwardly in an increasing amount as the level of reduced pressure between the cover and the wound increases.

16. The appliance of claim 12, wherein the protrusions are in the shape of hills or bumps.

17. The appliance of claim 12, wherein the protrusions are in the shape of a bellows.

18. The appliance of claim 12, wherein the protrusions have a color different from the color of the remaining surface of the cover, or a different shade of the same color as the shade of the color on the remaining surface of the cover, and wherein the color or the shade of the color of the protrusions changes as the protrusions are displaced away from the remaining surface of the cover.

19. The appliance of claim 12, further comprising sound means, wherein the sound means produce an audible sound as the protrusions are displaced away from the remaining surface of the cover.

20. The appliance of claim 12, further comprising:
a vacuum system adapted to produce a reduced pressure;
a collection system that is operably connected to the vacuum system; and
reduced pressure supply means for connection with the vacuum system adapted to supply the reduced pressure within the cover to the wound.

21. The appliance of claim 20, wherein the reduced pressure provided by the vacuum system is from about 2 in. Hg below atmospheric pressure to about 7 in. Hg below atmospheric pressure.

22. The appliance of claim 20, wherein the reduced pressure supply means comprises a length of tubing, and further comprising a flotation valve within the container for blocking the tubing when a predetermined amount of fluid is collected within the container.

23. The appliance of claim 12, wherein each of the plurality of protrusions has a closed end portion.

24. The appliance of claim 12, wherein the plurality of protrusions cover at least the majority of the cover.

25. The appliance of claim 12, wherein the plurality of protrusions cover substantially all of the cover.

26. The appliance of claim 12, wherein the cover is generally planar in use.

27. The appliance of claim 12, wherein the cover is a flexible sheet.

28. The appliance of claim 12, wherein each of the protrusions is spaced apart from the other protrusions such that no adjacent proximal protrusions are touching.

29. The appliance of claim 12, wherein the protrusions are configured to monitor the level of the pressure at the site of the body part being treated.

30. The appliance of claim 29, wherein the protrusions change color or change shade as a level of pressure exerted on the protrusions changes.

31. The appliance of claim 12, wherein at least some of the plurality of protrusions are configured to provide a visual indication of the level of the pressure at the site of the body part being treated by at least partially deflecting.

32. An appliance for administering a reduced pressure treatment to a wound, comprising:
a cover adapted to cover the wound and adapted to maintain reduced pressure in a space between the cover and the wound;
a conduit configured to supply a source of reduced pressure to the space between the cover and the wound; and
a pressure monitor supported by the cover and positioned so as to be separate and spaced apart from the conduit so that the pressure monitor is not in contact with the conduit;
wherein:

the pressure monitor comprises at least one surface that is configured to be exposed to the reduced pressure in the space between the cover and the wound; and the pressure monitor is configured to provide a visual indication of the level of reduced pressure between the cover and the wound such that a visual inspection of the appearance of the pressure monitor provides an indication of the level of reduced pressure in the space between the cover and the wound.

33. The appliance of claim 32, wherein the appliance further comprises an adhesive material on at least a portion of the cover, the adhesive material being adapted to at least secure a portion the cover to the tissue surrounding the wound.

34. The appliance of claim 32, further comprising a packing material adapted to prevent overgrowth of wound tissue, the packing material being located between the wound and the cover.

35. The appliance of claim 32, further comprising an absorbable matrix adapted to encourage growth of tissue in the area of the wound into the matrix, the matrix being located between the wound and the cover.

36. The appliance of claim 32, wherein the pressure monitor comprises one or more protrusions supported by the cover, each protrusion being configured to move between at least an expanded state and a compressed state, wherein each protrusion is configured to move toward the compressed state as the level of reduced pressure between the cover and the wound increases.

37. The appliance of claim 32, wherein the pressure monitor comprises one or more protrusions configured to be exposed to the reduced pressure in the space between the cover and the wound.

38. The appliance of claim 37, wherein each protrusion is in the shape of a hill or bump.

39. The appliance of claim 37, wherein each protrusion is in the shape of a bellows.

40. The appliance of claim 37, wherein each protrusion has a color different from the color of the remaining surface of the cover, or a different shade of the same color as the shade of the color on the remaining surface of the cover, and wherein the color or the shade of the color changes as the protrusion is displaced away from the remaining surface of the cover.

41. The appliance of claim 37, further comprising sound means, wherein the sound means produces an audible sound as the protrusion is displaced away from the remaining surface of the cover.

42. The appliance of claim 32, wherein the pressure monitor and the cover are formed so that the pressure monitor is integral with the cover.

43. The appliance of claim 32, further comprising a conduit comprising a first portion configured to communicate with a source of reduced pressure and comprising a second portion configured to communicate with the cover so that the conduit can transfer the reduced pressure supplied by the source of reduced pressure to the cover.

44. The appliance of claim 32, wherein the cover defines a periphery and the pressure monitor is positioned within the periphery of the cover.

45. The appliance of claim 32, wherein the cover is a flexible sheet.

46. The appliance of claim 32, wherein the pressure monitor comprises one or more protrusions supported by the cover, each protrusion being configured to displace in an increasing amount toward the wound as the level of reduced pressure between the cover and the wound increases.

47. The appliance of claim 32, further comprising a pump configured to provide reduced pressure to the space between the cover and the wound.

48. The appliance of claim 32, wherein the pressure monitor is configured to indicate when a predetermined level of reduced pressure is achieved in the space between the cover and the wound.

49. An appliance for administering a reduced pressure treatment to a wound, comprising a cover adapted to cover the wound so as to maintain reduced pressure at the site of the wound, wherein the cover comprises a plurality of protrusions positioned across an outside surface of the cover arranged so as to project away from the outside surface of the cover, the plurality of protrusions covering at least the majority of the outside surface of the cover and each having an inside surface that is configured to be in direct communication with the reduced pressure beneath the cover.

50. The appliance of claim 49, wherein the plurality of protrusions cover an area of the outside surface of the cover at least as large as the area of the wound.

51. The appliance of claim 49, wherein the plurality of protrusions have a bellows-type configuration.

52. The appliance of claim 49, wherein the plurality of protrusions are configured to displace inwardly as the reduced pressure between the cover and the wound increases.

53. The appliance of claim 49, wherein the plurality of protrusions supported by the cover are configured to displace inwardly in an increasing amount as the level of reduced pressure between the cover and the wound increases.

54. The appliance of claim 49, wherein the appliance further comprises an adhesive material on at least a portion of the cover, the adhesive material being adapted to at least secure a portion the cover to tissue surrounding the wound.

55. The appliance of claim 49, further comprising a packing material adapted to prevent overgrowth of wound tissue, the packing material being located between the wound and the cover.

56. The appliance of claim 49, further comprising an absorbable matrix adapted to encourage growth of tissue in the area of the wound into the matrix, the matrix being located between the wound and the cover.

57. The appliance of claim 49, further comprising:
a vacuum system adapted to produce a reduced pressure;
a collection system that is operably connected to the vacuum system, and
reduced pressure supply means for connection with the vacuum system adapted to supply the reduced pressure within the cover to the wound.

58. The appliance of claim 57, wherein the reduced pressure provided by the vacuum system is from about 2 in. Hg below atmospheric pressure to about 7 in. Hg below atmospheric pressure.

59. The appliance of claim 49, wherein at least some of the protrusions have a color that is different than the color of the remaining surface of the cover, or the protrusions have a different shade of the same color as the remaining surface of the cover.

60. An appliance for administering a reduced pressure treatment to a wound, comprising:
a wound dressing comprising:
a cover adapted to cover the wound and adapted to maintain reduced pressure in a space between the cover and the wound; and
a pressure monitor comprising a protrusion protruding above a surface of the cover and configured to be displaced downward to provide a visual indication of reduced pressure being applied beneath the cover;

a vacuum pump; and a conduit configured to connect the vacuum pump to the dressing.

61. The appliance of claim 60, wherein the pressure monitor is supported by the cover and spaced and positioned so as to be separate and spaced apart from the conduit so that the pressure monitor is not in contact with the conduit.

62. The appliance of claim 60, wherein the pressure monitor comprises at least one surface that is configured to be exposed to the reduced pressure in the space between the cover and the wound.

63. The appliance of claim 60, further comprising a collection container in communication with the vacuum pump.

64. The appliance of claim 63, wherein the collection container includes a shutoff mechanism for halting the supply of reduced pressure to the appliance in the event that exudate aspirated from the wound exceeds a predetermined quantity.

65. The appliance of claim 60, wherein the cover is a flexible, fluid impermeable cover.

66. The appliance of claim 60, wherein the cover comprises adhesive.

67. The appliance of claim 60, further comprising foam sized and configured to be placed under the wound dressing at the site of the wound.

68. The appliance of claim 60, wherein the pressure monitor is configured to be displaced downward when a predetermined level of reduced pressure is achieved beneath the cover.

* * * * *